(12) United States Patent
Li et al.

(10) Patent No.: US 11,344,199 B2
(45) Date of Patent: May 31, 2022

(54) SYSTEMS AND METHODS FOR DETECTION AND PREDICTION OF BRAIN DISORDERS BASED ON NEURAL NETWORK INTERACTION

(75) Inventors: Shi-Jiang Li, Brookfield, WI (US); Gang Chen, Wauwatosa, WI (US); Barney D. Ward, West Allis, WI (US); Zhilin Wu, Milwaukee, WI (US); Piero Antuono, Wauwatosa, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 0 days.

(21) Appl. No.: 13/634,284

(22) PCT Filed: Mar. 15, 2011

(86) PCT No.: PCT/US2011/028459
§ 371 (c)(1),
(2), (4) Date: Jan. 22, 2013

(87) PCT Pub. No.: WO2011/115956
PCT Pub. Date: Sep. 22, 2011

(65) Prior Publication Data
US 2013/0116540 A1    May 9, 2013

Related U.S. Application Data

(60) Provisional application No. 61/432,103, filed on Jan. 12, 2011, provisional application No. 61/313,983, filed on Mar. 15, 2010.

(51) Int. Cl.
*A61B 5/00* (2006.01)
*A61B 5/055* (2006.01)
(Continued)

(52) U.S. Cl.
CPC ............ *A61B 5/0042* (2013.01); *A61B 5/055* (2013.01); *A61B 5/4064* (2013.01);
(Continued)

(58) Field of Classification Search
CPC ......... A61B 5/00; A61B 5/055; A61B 5/4088; A61B 5/0042; A61B 5/4064; A61B 5/7264; A61B 5/7267; A61B 5/7246
(Continued)

(56) References Cited

U.S. PATENT DOCUMENTS 5,603,322 A * 2/1997 Jesmanowicz et al. ...... 600/410
6,490,472 B1   12/2002 Li et al.
(Continued)

OTHER PUBLICATIONS

Wang et al. "Discriminative Analysis of Early Alzheimer's Disease Based on Two Intrinsically Anti-correlated Networks with Resting-State fMRI." MICCAI 2006, LNCS 4191, pp. 340-347, 2006 (Year: 2006).*

(Continued)

*Primary Examiner* — Luther Behringer
(74) *Attorney, Agent, or Firm* — Quarles & Brady LLP

(57) ABSTRACT

Systems and methods obtain functional connectivity data in the whole brain to detect and predict brain disorders. This whole brain data is regionalized and then manipulated to derive functional connectivity data sets that can be used to show measured functional connectivity changes. This whole brain data may also be analyzed to determine changes in functional activity in both increased and decreased neural network connectivity. By identifying and then quantifying the functional connectivity differences between healthy and diseased subjects, a classification for individual subjects can be made.

17 Claims, 19 Drawing Sheets

(51) Int. Cl.
  *G01R 33/48* (2006.01)
  *G06T 7/00* (2017.01)
  *G16H 50/70* (2018.01)

(52) U.S. Cl.
  CPC .......... *A61B 5/4088* (2013.01); *A61B 5/7246* (2013.01); *A61B 5/7264* (2013.01); *G01R 33/4806* (2013.01); *G06T 7/0016* (2013.01); *G16H 50/70* (2018.01); *A61B 5/7267* (2013.01); *G06T 2207/10016* (2013.01); *G06T 2207/10088* (2013.01); *G06T 2207/30016* (2013.01)

(58) Field of Classification Search
  USPC .......................................................... 600/410
  See application file for complete search history.

(56) References Cited

U.S. PATENT DOCUMENTS

| | | | |
|---|---|---|---|
| 7,511,472 B1 | 8/2009 | Li et al. | |
| 2005/0085705 A1* | 4/2005 | Rao | A61B 5/055 |
| | | | 600/345 |
| 2005/0215884 A1* | 9/2005 | Greicius et al. | 600/410 |
| 2006/0241382 A1 | 10/2006 | Li et al. | |
| 2008/0091118 A1* | 4/2008 | Georgopoulos | A61B 5/04008 |
| | | | 600/544 |
| 2008/0133141 A1 | 6/2008 | Frost | |
| 2008/0292194 A1* | 11/2008 | Schmidt et al. | 382/217 |
| 2009/0035766 A1 | 2/2009 | Khan et al. | |
| 2009/0075395 A1* | 3/2009 | Lee et al. | 436/513 |

OTHER PUBLICATIONS

Gang et al. "Classification of Alzheimer Disease Mild Cognitive Impairment and Normal Cognitive Status with Large Scale Network Analysis based on Resting-State fMRI." Radiology: vol. 259: No. 1—Apr. 2011 (Year: 2011).*

Colliot et al. "Discrimination between Alzheimer's disease, mild cognitive impairment and normal aging by using automated segmentation of the hippocampus." Radiology, Jul. 2008;248(1):194-201. (Year: 2008).*

Supekar, Kaustubh et al. "Network analysis of intrinsic functional brain connectivity in Alzheimer's disease." PLoS computational biology vol. 4,6 e1000100. Jun. 27, 2008. (Year: 2008).*

International Search Report and Written Opinion under dated May 18, 2011 in connection with PCT/US2011/028459.

* cited by examiner

| Classification result between AD vs. non-AD subjects in the first step. |||
|---|---|---|
| Step 1 | AD (20) | Non AD (35) |
| Classified as AD | 85% (17) | 20% (7) |
| Classified as Non AD | 15% (3) | 80% (28) |

FIG. 14A

| Classification result between aMCI subjects vs. CN subjects in the second step. ||||
|---|---|---|---|
| Step 2 | AD (3) from step 1 | aMCI (15) | CN (20) |
| Classified as aMCI | (2) | 93% (14), including 3 AD from step 1 | 10% (2), including 1 AD from step 1 |
| Classified as CN | (1) | 7% (1) | 90% (18), including 3 AD from step 1 |

FIG. 14B

| Combined result from the two-step tri-group classification. ||||
|---|---|---|---|
| Subjects | AD (20) | aMCI (15) | CN (20) |
| Classified as AD | 85% (17) | 20% (3) | 20% (4) |
| Classified as aMCI | 10% (2) | 73% (11) | 5% (1) |
| Classified as CN | 5% (1) | 7% (1) | 75% (15) |

FIG. 14C

| Classification result between diseased (both AD and aMCI) vs. CN subjects. ||||
|---|---|---|---|
| Subjects | AD (20) | aMCI (15) | CN (20) |
| Classified as diseased | 95% (19) | 93% (14) | 25% (5) |
| Classified as non diseased | 5% (1) | 7% (1) | 75% (15) |

FIG. 14D

| | | # connections in Decreased Connection Set | | | | | | | | | | | | | | | | | | | |
|---|---|---|---|---|---|---|---|---|---|---|---|---|---|---|---|---|---|---|---|---|---|---|
| | AUC | 0 | 1 | 2 | 3 | 4 | 5 | 6 | 8 | 10 | 15 | 20 | 30 | 40 | 60 | 80 | 100 | 150 | 200 | 250 | 300 | 350 | 400 |
| # connections in Increase Connection Set | 0 | N/A | 0.58 | 0.70 | 0.76 | 0.68 | 0.71 | 0.66 | 0.67 | 0.65 | 0.75 | 0.78 | 0.74 | 0.74 | 0.76 | 0.76 | 0.80 | 0.77 | 0.77 | 0.80 | 0.85 | 0.85 | 0.86 |
| | 1 | 0.81 | 0.85 | 0.86 | 0.88 | 0.89 | 0.89 | 0.87 | 0.81 | 0.80 | 0.83 | 0.86 | 0.84 | 0.82 | 0.81 | 0.82 | 0.85 | 0.83 | 0.85 | 0.86 | 0.89 | 0.89 | 0.89 |
| | 2 | 0.93 | 0.91 | 0.90 | 0.92 | 0.93 | 0.91 | 0.91 | 0.83 | 0.85 | 0.86 | 0.87 | 0.86 | 0.84 | 0.83 | 0.84 | 0.86 | 0.85 | 0.84 | 0.86 | 0.88 | 0.88 | 0.88 |
| | 3 | 0.83 | 0.84 | 0.85 | 0.87 | 0.82 | 0.84 | 0.83 | 0.81 | 0.80 | 0.84 | 0.84 | 0.82 | 0.81 | 0.79 | 0.79 | 0.83 | 0.82 | 0.82 | 0.84 | 0.87 | 0.87 | 0.88 |
| | 4 | 0.73 | 0.73 | 0.75 | 0.80 | 0.78 | 0.77 | 0.75 | 0.74 | 0.75 | 0.79 | 0.80 | 0.78 | 0.76 | 0.77 | 0.78 | 0.81 | 0.79 | 0.79 | 0.82 | 0.86 | 0.86 | 0.86 |
| | 5 | 0.73 | 0.75 | 0.76 | 0.79 | 0.78 | 0.76 | 0.73 | 0.73 | 0.73 | 0.78 | 0.79 | 0.78 | 0.76 | 0.77 | 0.78 | 0.81 | 0.78 | 0.78 | 0.81 | 0.86 | 0.86 | 0.86 |
| | 6 | 0.80 | 0.81 | 0.80 | 0.84 | 0.83 | 0.81 | 0.79 | 0.78 | 0.78 | 0.81 | 0.82 | 0.80 | 0.78 | 0.78 | 0.79 | 0.82 | 0.79 | 0.80 | 0.83 | 0.87 | 0.87 | 0.87 |
| | 8 | 0.81 | 0.82 | 0.80 | 0.81 | 0.78 | 0.81 | 0.79 | 0.78 | 0.78 | 0.81 | 0.81 | 0.81 | 0.78 | 0.79 | 0.80 | 0.82 | 0.81 | 0.81 | 0.85 | 0.87 | 0.87 | 0.87 |
| | 10 | 0.81 | 0.78 | 0.80 | 0.79 | 0.80 | 0.78 | 0.79 | 0.77 | 0.78 | 0.82 | 0.83 | 0.81 | 0.79 | 0.79 | 0.80 | 0.83 | 0.82 | 0.82 | 0.84 | 0.87 | 0.88 | 0.88 |
| | 15 | 0.78 | 0.76 | 0.76 | 0.79 | 0.73 | 0.73 | 0.78 | 0.77 | 0.78 | 0.81 | 0.81 | 0.80 | 0.78 | 0.79 | 0.79 | 0.82 | 0.79 | 0.80 | 0.83 | 0.87 | 0.87 | 0.87 |
| | 20 | 0.81 | 0.80 | 0.81 | 0.84 | 0.82 | 0.80 | 0.79 | 0.79 | 0.80 | 0.82 | 0.82 | 0.81 | 0.80 | 0.79 | 0.80 | 0.83 | 0.80 | 0.81 | 0.83 | 0.87 | 0.87 | 0.87 |
| | 30 | 0.85 | 0.83 | 0.83 | 0.84 | 0.83 | 0.82 | 0.81 | 0.81 | 0.81 | 0.82 | 0.83 | 0.82 | 0.81 | 0.80 | 0.81 | 0.83 | 0.81 | 0.82 | 0.83 | 0.88 | 0.87 | 0.87 |
| | 40 | 0.76 | 0.78 | 0.77 | 0.77 | 0.77 | 0.76 | 0.77 | 0.77 | 0.77 | 0.78 | 0.79 | 0.79 | 0.77 | 0.77 | 0.79 | 0.80 | 0.79 | 0.80 | 0.82 | 0.85 | 0.84 | 0.85 |
| | 60 | 0.77 | 0.77 | 0.77 | 0.77 | 0.77 | 0.77 | 0.76 | 0.77 | 0.77 | 0.77 | 0.79 | 0.79 | 0.77 | 0.77 | 0.79 | 0.80 | 0.79 | 0.79 | 0.81 | 0.84 | 0.84 | 0.84 |
| | 80 | 0.82 | 0.81 | 0.80 | 0.81 | 0.80 | 0.80 | 0.80 | 0.81 | 0.81 | 0.81 | 0.81 | 0.81 | 0.80 | 0.80 | 0.80 | 0.81 | 0.80 | 0.80 | 0.81 | 0.85 | 0.85 | 0.85 |
| | 100 | 0.82 | 0.81 | 0.80 | 0.81 | 0.81 | 0.81 | 0.81 | 0.81 | 0.81 | 0.82 | 0.81 | 0.82 | 0.81 | 0.81 | 0.80 | 0.81 | 0.81 | 0.80 | 0.81 | 0.85 | 0.85 | 0.85 |
| | 150 | 0.80 | 0.80 | 0.78 | 0.78 | 0.79 | 0.79 | 0.80 | 0.80 | 0.80 | 0.80 | 0.80 | 0.80 | 0.79 | 0.79 | 0.80 | 0.81 | 0.80 | 0.80 | 0.80 | 0.83 | 0.82 | 0.83 |
| | 200 | 0.75 | 0.76 | 0.72 | 0.71 | 0.74 | 0.74 | 0.75 | 0.75 | 0.75 | 0.75 | 0.75 | 0.76 | 0.75 | 0.77 | 0.77 | 0.78 | 0.77 | 0.77 | 0.77 | 0.79 | 0.79 | 0.79 |
| | 250 | 0.73 | 0.74 | 0.71 | 0.68 | 0.71 | 0.72 | 0.73 | 0.73 | 0.73 | 0.74 | 0.73 | 0.74 | 0.75 | 0.75 | 0.75 | 0.76 | 0.76 | 0.75 | 0.76 | 0.78 | 0.79 | 0.79 |
| | 300 | 0.75 | 0.75 | 0.74 | 0.71 | 0.74 | 0.74 | 0.75 | 0.75 | 0.75 | 0.75 | 0.75 | 0.76 | 0.75 | 0.77 | 0.77 | 0.78 | 0.77 | 0.76 | 0.77 | 0.79 | 0.79 | 0.79 |
| | 350 | 0.76 | 0.77 | 0.75 | 0.72 | 0.76 | 0.76 | 0.77 | 0.76 | 0.77 | 0.77 | 0.76 | 0.77 | 0.76 | 0.77 | 0.77 | 0.77 | 0.77 | 0.77 | 0.78 | 0.80 | 0.79 | 0.79 |
| | 400 | 0.79 | 0.79 | 0.78 | 0.76 | 0.78 | 0.79 | 0.80 | 0.79 | 0.79 | 0.78 | 0.79 | 0.79 | 0.79 | 0.79 | 0.79 | 0.79 | 0.79 | 0.79 | 0.80 | 0.82 | 0.81 | 0.81 |

FIG. 17

| | | # connections in Decreased Connection Set | | | | | | | | | | | | | | | | | |
|---|---|---|---|---|---|---|---|---|---|---|---|---|---|---|---|---|---|---|---|
| | AUC | 0 | 1 | 2 | 3 | 4 | 5 | 6 | 8 | 10 | 15 | 20 | 30 | 40 | 60 | 80 | 100 | 120 | 150 | 200 |
| # connections in Increase Connection Set | 0 | 0.00 | 0.85 | 0.71 | 0.70 | 0.85 | 0.82 | 0.84 | 0.76 | 0.71 | 0.61 | 0.57 | 0.63 | 0.52 | 0.39 | 0.41 | 0.40 | 0.36 | 0.35 | 0.35 |
| | 1 | 0.77 | 0.87 | 0.75 | 0.81 | 0.88 | 0.83 | 0.81 | 0.75 | 0.77 | 0.67 | 0.62 | 0.68 | 0.58 | 0.44 | 0.48 | 0.46 | 0.42 | 0.41 | 0.40 |
| | 2 | 0.85 | 0.96 | 0.89 | 0.91 | 0.95 | 0.92 | 0.83 | 0.81 | 0.77 | 0.74 | 0.68 | 0.75 | 0.64 | 0.56 | 0.60 | 0.54 | 0.53 | 0.50 | 0.48 |
| | 3 | 0.70 | 0.85 | 0.80 | 0.85 | 0.88 | 0.82 | 0.81 | 0.77 | 0.73 | 0.72 | 0.68 | 0.74 | 0.64 | 0.53 | 0.57 | 0.54 | 0.51 | 0.51 | 0.49 |
| | 4 | 0.70 | 0.83 | 0.77 | 0.81 | 0.82 | 0.83 | 0.81 | 0.79 | 0.77 | 0.69 | 0.66 | 0.70 | 0.63 | 0.52 | 0.55 | 0.52 | 0.50 | 0.48 | 0.48 |
| | 5 | 0.63 | 0.76 | 0.73 | 0.77 | 0.78 | 0.77 | 0.83 | 0.78 | 0.74 | 0.66 | 0.63 | 0.66 | 0.59 | 0.49 | 0.52 | 0.50 | 0.48 | 0.43 | 0.42 |
| | 6 | 0.65 | 0.77 | 0.69 | 0.74 | 0.81 | 0.81 | 0.79 | 0.76 | 0.70 | 0.63 | 0.59 | 0.61 | 0.56 | 0.46 | 0.47 | 0.45 | 0.43 | 0.42 | 0.41 |
| | 8 | 0.45 | 0.65 | 0.59 | 0.62 | 0.71 | 0.71 | 0.69 | 0.65 | 0.62 | 0.53 | 0.52 | 0.54 | 0.48 | 0.38 | 0.43 | 0.40 | 0.39 | 0.38 | 0.38 |
| | 10 | 0.36 | 0.56 | 0.48 | 0.52 | 0.60 | 0.62 | 0.60 | 0.57 | 0.54 | 0.46 | 0.46 | 0.48 | 0.44 | 0.37 | 0.39 | 0.37 | 0.36 | 0.35 | 0.35 |
| | 15 | 0.34 | 0.51 | 0.47 | 0.47 | 0.57 | 0.55 | 0.55 | 0.54 | 0.51 | 0.44 | 0.44 | 0.49 | 0.46 | 0.35 | 0.38 | 0.37 | 0.36 | 0.35 | 0.35 |
| | 20 | 0.42 | 0.59 | 0.49 | 0.50 | 0.59 | 0.59 | 0.58 | 0.56 | 0.55 | 0.47 | 0.46 | 0.49 | 0.47 | 0.38 | 0.39 | 0.38 | 0.37 | 0.35 | 0.36 |
| | 30 | 0.42 | 0.58 | 0.48 | 0.49 | 0.57 | 0.58 | 0.56 | 0.55 | 0.55 | 0.49 | 0.48 | 0.51 | 0.46 | 0.40 | 0.42 | 0.41 | 0.39 | 0.38 | 0.38 |
| | 40 | 0.45 | 0.55 | 0.48 | 0.53 | 0.60 | 0.58 | 0.57 | 0.57 | 0.57 | 0.53 | 0.55 | 0.54 | 0.47 | 0.40 | 0.42 | 0.42 | 0.40 | 0.38 | 0.40 |
| | 60 | 0.42 | 0.56 | 0.51 | 0.50 | 0.54 | 0.51 | 0.52 | 0.51 | 0.50 | 0.48 | 0.46 | 0.47 | 0.47 | 0.41 | 0.43 | 0.42 | 0.41 | 0.39 | 0.38 |
| | 80 | 0.38 | 0.54 | 0.45 | 0.46 | 0.49 | 0.47 | 0.47 | 0.45 | 0.46 | 0.44 | 0.43 | 0.44 | 0.43 | 0.37 | 0.38 | 0.36 | 0.36 | 0.34 | 0.34 |
| | 100 | 0.41 | 0.61 | 0.51 | 0.52 | 0.57 | 0.52 | 0.53 | 0.51 | 0.50 | 0.47 | 0.48 | 0.48 | 0.45 | 0.39 | 0.41 | 0.39 | 0.40 | 0.38 | 0.37 |
| | 120 | 0.46 | 0.64 | 0.54 | 0.56 | 0.59 | 0.55 | 0.56 | 0.55 | 0.53 | 0.49 | 0.49 | 0.52 | 0.49 | 0.43 | 0.45 | 0.45 | 0.45 | 0.42 | 0.40 |
| | 150 | 0.43 | 0.61 | 0.51 | 0.51 | 0.56 | 0.53 | 0.53 | 0.52 | 0.51 | 0.49 | 0.49 | 0.51 | 0.47 | 0.42 | 0.45 | 0.44 | 0.42 | 0.40 | 0.39 |
| | 200* | 0.58 | 0.72 | 0.63 | 0.62 | 0.68 | 0.64 | 0.65 | 0.62 | 0.60 | 0.56 | 0.57 | 0.55 | 0.53 | 0.46 | 0.49 | 0.48 | 0.46 | 0.44 | 0.44 |

FIG. 18

SYSTEMS AND METHODS FOR DETECTION AND PREDICTION OF BRAIN DISORDERS BASED ON NEURAL NETWORK INTERACTION

CROSS-REFERENCE TO RELATED APPLICATIONS

This application represents the national stage entry of PCT International Application No. PCT/US2011/028459 filed Mar. 15, 2011, which claims the benefit of provisional application Ser. No. 61/313,983, filed Mar. 15, 2010, and entitled "SYSTEMS AND METHODS FOR DETECTION AND PREDICTION OF BRAIN DISORDERS BASED ON NEURAL NETWORK INTERACTION," which is hereby incorporated by reference.

This application also claims the benefit of provisional application Ser. No. 61/432,103, filed Jan. 12, 2011, and entitled "SYSTEMS AND METHODS FOR DETECTION AND PREDICTION OF BRAIN DISORDERS BASED ON NEURAL NETWORK INTERACTION," all of which are hereby incorporated by reference.

STATEMENT CONCERNING FEDERALLY SPONSORED RESEARCH OR DEVELOPMENT

This invention was made with government support under Grant No. AG020279 awarded by the National Institute of Health. The government has certain rights in the invention.

BACKGROUND OF THE INVENTION

The field of the invention is the prediction and detection of neurodegenerative brain disorders using medical imaging techniques. More particularly, the invention relates to systems and methods for the prediction and detection of neurodegenerative brain disorders based on neural network interaction.

When a substance such as human tissue is subjected to a uniform magnetic field (polarizing field $B_0$), the individual magnetic moments of the excited nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_t$. A signal is emitted by the excited nuclei or "spins", after the excitation signal $B_1$ is terminated, and this signal may be received and processed to form an image.

One form of medical imaging is functional magnetic resonance imaging (fMRI), and fMRI technology provides an approach to study neuronal activity. Conventional fMRI detects changes in cerebral blood volume, flow, and oxygenation that locally occur in association with increased neuronal activity induced by functional paradigms. As described in U.S. Pat. No. 5,603,322, an MRI system is used to acquire signals from the brain over a period of time. As the brain performs a task, these signals are modulated synchronously with task performance to reveal which regions of the brain are involved in performing the task. Recently, brain activity may be monitored over a resting state without performing any required task. In either case, the series of fMRI time course images must be acquired at a rate that is high enough to see changes in brain activity. In addition, because neuronal activity may occur at widely dispersed locations in the brain, a relatively large 3D volume or multi-slice volume must be acquired in each time frame.

Conventional fMRI is currently being used as a means for detection of neurodegenerative diseases, yet even with the benefits of fMRI technology, these neurodegenerative diseases are difficult to quantify, and the outcomes of fMRI don't necessarily provide complete information necessary to make an assessment. Due to their severity, significant efforts in a variety of modalities to diagnose and treat these diseases are underway.

One example of a neurodegenerative disease that is receiving much attention is Alzheimer's disease (AD). Alzheimer's disease is a devastating disease of the brain that results in progressive dementia, physical disability and death over a relatively long period of time. With the aging population in the United States and other countries, the number of Alzheimer's subjects is rapidly rising and can accurately be characterized as a silent epidemic. Alzheimer's disease is the seventh-leading cause of death in the United States. Although substantial progress has been made in unraveling the causes and pathophysiology of AD, developing animal models, and designing novel therapeutic strategies, there is still great interest in developing objective biologically based markers that can be used to predict AD risk, diagnose, track the disease progression, and monitor efficacy of the disease treatment.

One of the difficulties in managing this disease is the lack of means for its early detection and means for measuring its progression. Such means are needed to identify persons who should receive treatment and to measure the effectiveness of the treatment. An immediate problem is the need for systems and methods that measure the progression of the disease in order to evaluate the effectiveness of the many drugs being developed.

Many techniques have been proposed for detecting and measuring the progress of Alzheimer's disease. These include cognitive tests which attempt to measure brain functions by having the subject perform different tasks. The problem with this approach is that it does not distinguish between dementia caused by Alzheimer's disease and dementia caused by other factors. In addition, the ability to measure the progression of the disease using cognitive tests is very limited.

The formation of senile plaques and neurofibrillary tangles (NFTs) has been believed to be the core mechanism of Alzheimer's disease. Amyloid imaging represents a major advance in AD research, thereby enabling the detection and quantification of pathologic protein aggregations in the brain. As recently reviewed, [$^{11}$C] Pittsburgh compound B (PIB) positron emission tomography (PIB-PET) provides us with a powerful tool to examine in vivo the relationship between amyloid deposition, clinical symptoms, and structural and functional brain changes in the continuum between normal aging and AD. However, the PIB-PET approach is not very effective for typical late onset Alzheimer's disease because amyloid deposition proceeds at a constant slow rate while neurodegeneration accelerates and clinical symptoms are coupled to neurodegeneration, not amyloid deposition. In addition, plaques and tangles are commonly encountered in individuals who are not clinically demented.

[$^{18}$F] fluorodeoxyglucose (FDG), which has been used in PET to measure metabolism, was found to be better related to cognition than the cerebrospinal fluid (CSF) and PIB methods. By taking advantage of both amyloid imaging of PIB-PET and structural atrophy imaging with MRI, a complementary role for MRI and PIB imaging in AD has been proposed. Despite these advances to characterize AD, limited progress has been made in terms of the development of an imaging marker in vivo for identifying, distinguishing, and tracking neurodegenerative and other cognitive losses.

In the quest for early AD biomarkers, the "resting-state" functional magnetic resonance imaging (R-fMRI) method has been employed. "Resting state" refers to study subjects who do not perform any tasks or respond to any stimulus during scanning. R-fMRI provides new insights into how structurally segregated and functionally specialized brain networks are interconnected. A new network dysfunction perspective on neurodegenerative diseases has been recently proposed. Several previous studies have focused on specific hypotheses-driven tests such as hippocampus networks, default mode networks, or using global network properties, such as the clustering coefficient and characteristic path length in the small-world network analysis. These studies provided a new, large-scale view of the neural network of the brain's intrinsic activity. So far, however, these approaches have limited success to classify AD, mild cognitive impairment (MCI), and cognitively normal (CN) subjects in a meaningful way at the single-subject level. A more sophisticated analysis of the large-scale network (LSN) patterns of brain's intrinsic activity is needed.

With regard to the hippocampus, it has been suggested that with progression of Alzheimer's disease, the increased presence of senile plaques and NFTs in the hippocampus disrupt the perforant pathway and affect functional connectivity. A number of methods have been proposed to assess the functional connectivity in the hippocampal region. However, in practical terms, all these approaches have limited classification capability to provide high accuracy.

As previously discussed, fMRI has provided a new approach to study neuronal activity. As the brain performs a task, brain signals are modulated synchronously with task performance to reveal which regions of the brain are involved in performing the task. Much research has been done to find tasks which can be performed by subjects, and which reveal in an fMRI image acquired at the same time, regions in the brain that function differently when Alzheimer's disease is present.

In U.S. Pat. No. 6,490,472, an fMRI method is described for producing an indication of the presence and the progress of a brain disorder by measuring the functional connectivity in the hippocampus while the brain is substantially at rest. An index called Cross-correlation Coefficients of Spontaneous Low Frequency (the "COSLOF" index) is calculated from the time course fMRI data acquired from a selected region of the brain and a strong correlation was found between this index and the presence of Alzheimer's disease.

It has been suggested that the COSLOF index method has two limitations. First, it is very difficult to accurately identify the voxels in the brain that should be included in the calculation of the index. And second, the signal-to-noise ratio of the acquired Blood-Oxygen-Level-Dependent (BOLD) signal at the resting condition is very low and this impairs the accurate calculation of the COSLOF index. As a result, the COSLOF index is useful in identifying subjects with Alzheimer's disease, but it is not sensitive enough to identify subjects with mild cognitive impairment (MCI) who will eventually evidence Alzheimer's disease. The identification of MCI subjects is very important, since it is these subjects who should receive treatment before Alzheimer's disease more significantly impairs the brain.

In U.S. Pat. No. 7,577,472, a new fMRI method is described for overcoming the limitations of the COSLOF index method. The method includes a high spatial and temporal resolution and computer software to quantify synchronization and rhythmic processes in the human brain, with whole brain coverage. This method allows the determination of baseline human brain function as opposed to the previous BOLD contrast that was only suitable for relative changes. However, the method can be insufficient when attempting to consider classification and quantification of neurodegenerative and other cognitive losses, such as for AD, amnestic MCI (aMCI), and cognitively normal (CN) subjects, while using large-scale brain functional connectivity differences.

Therefore, it would be desirable to have systems and methods that are capable of quantifying the development of brain disorders, such as AD and aMCI, and age matched CN subjects. A data-driven approach should be used to examine the large-scale brain functional connectivity differences among clinically defined groups of subjects to show that disease-altered functional connectivity can be employed to classify AD, aMCI and age-matched CN subjects, for example. Such an objective classification could be used to assist clinicians in either strongly confirming or ruling out their clinical assessment.

SUMMARY OF THE INVENTION

The present invention includes systems and methods for producing indices used for classifying and quantifying the presence and the progress, or lack thereof, of disorders in the brain, including diseases, physical and/or mental abnormalities, or trauma, for example, by measuring the functional connectivity changes in the whole human brain. More specifically, the present invention is an improvement in prior systems and methods in that it uses a data-driven, large-scale network (LSN) approach to examine the functional connectivity in the whole human brain and classify and quantify differences among groups of subjects, such as with AD, aMCI, and age-matched CN subjects.

One aspect of the invention is an improved system and method for classifying the brain of a subject into a class based on presence or progression or lack of a brain disorder. Embodiments of the systems and methods include a processor that is operable to access time course image data from memory. The processor is programmed to perform the steps of: a) acquiring with a medical imaging system time course image data from the brain of the subject; b) determining a functional connectivity in the brain of the subject between at least a set of functional regions of interest, from the time course image data acquired in step a); c) comparing the functional connectivity in the brain of the subject measured in step b) with at least one class classifier, the class classifier including an increased functional connectivity at the at least a set of functional regions of interest and/or a decreased functional connectivity at the at least a set of functional regions of interest; and d) classifying the subject into at least one class based on step c).

Embodiments of the invention enable an imaging system to obtain functional data in the whole brain. This whole brain data is then regionalized into a number of regions, and then manipulated to derive regional functional connectivity data sets that can be used to determine regions that have functional connectivity changes among groups of subjects. Single subject whole brain data may then be analyzed to determine functional connectivity indices in these regions. It has been discovered that these measured connectivity indices correlate strongly with established behavioral scores, and can be utilized to classify subjects with AD, those with aMCI, and CN subjects. Embodiments of the invention may also be used to define functional connectivity indices that allow for meaningful and individualized diagnosis of AD onset, progression, and response to treatment. Embodiments of the invention also provide improved systems and methods for applying a biomarker for other physical and/or mental disorders such as frontotemporal dementia, vascular dementia, epilepsy, autism, depression, schizophrenia, concussion, and other brain disorders.

In one embodiment, a decreased connectivity index (DCI) and an increased connectivity index (ICI) may be produced. These indices may then be used in a classification algorithm to determine whether the presence of a disorder in the brain of the subject can be detected.

BRIEF DESCRIPTION OF THE DRAWINGS

FIGS. 14A to 14D are tables that summarize classification results in one example;

FIG. 17 is a table that shows the number of connections includes in the decreased and increased connection set for classifying AD from non-AD groups; and FIG. 18 is a table that shows the number of connections includes in the decreased and increased connection set for classifying aMCI from CN groups.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENT

The various aspects of the invention will be described in connection with the detection and prediction of brain disorders based on neural network interaction. That is because the features and advantages that arise due to the invention are well suited to this purpose. Still, it should be appreciated that the various aspects of the invention can be applied to achieve other objectives as well.

Figure 1:
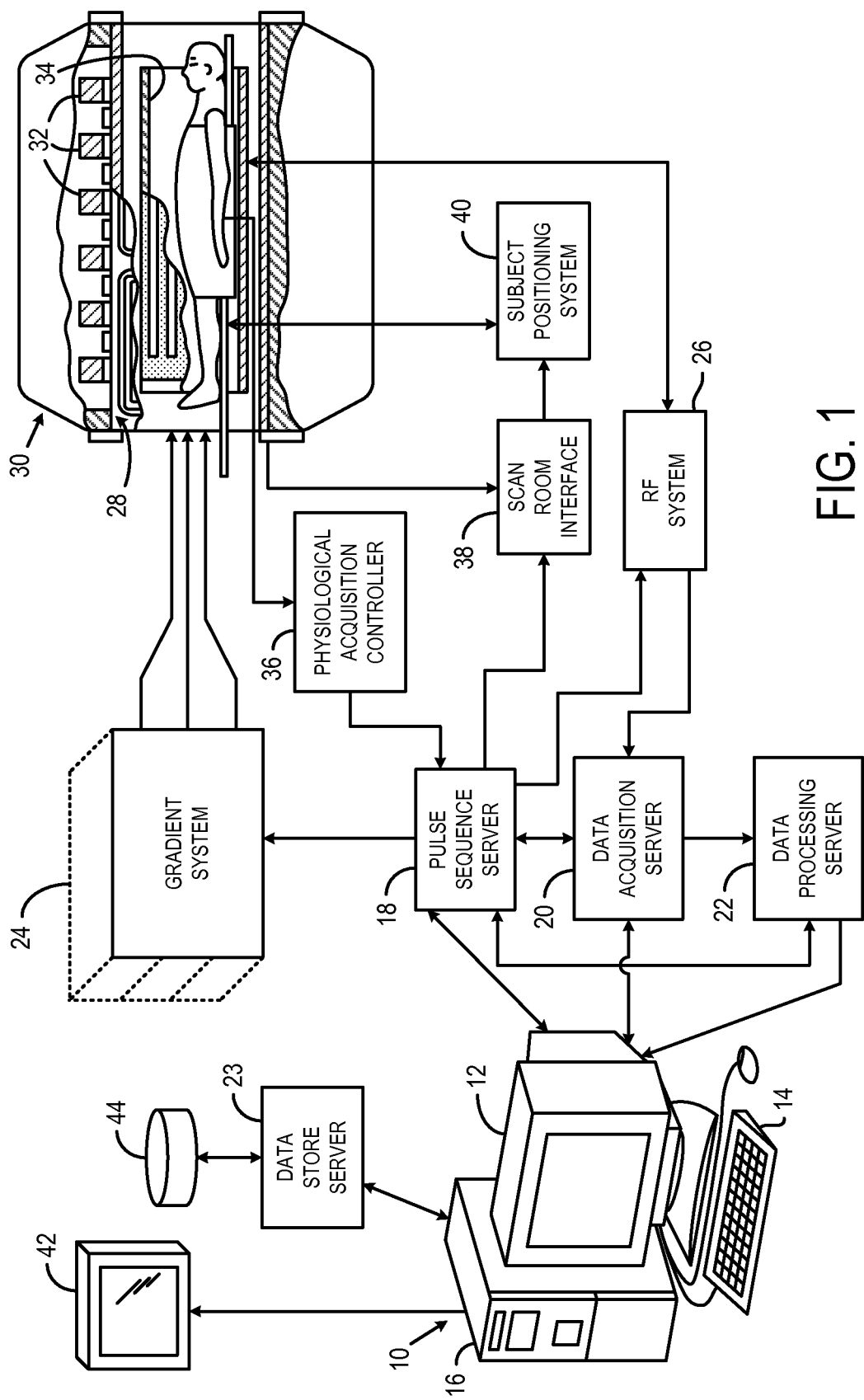
FIG. 1 is a block diagram of an MRI system usable with embodiments of the present invention.

Referring to FIG. 1, embodiments of the present invention may employ an MRI system. The MRI system includes a workstation 10 having a display 12 and a keyboard 14. The workstation 10 includes a processor 16 that is a commercially available programmable machine running a commercially available operating system. The workstation 10 provides the operator interface that enables scan prescriptions to be entered into the MRI system. The workstation 10 is coupled to four servers including a pulse sequence server 18, a data acquisition server 20, a data processing server 22, and a data store server 23. The workstation 10 and each server 18, 20, 22 and 23 are connected to communicate with each other.

The pulse sequence server 18 functions in response to instructions downloaded from the workstation 10 to operate a gradient system 24 and an radio frequency (RF) system 26. Gradient waveforms necessary to perform the prescribed scan are produced and applied to the gradient system 24 that excites gradient coils in an assembly 28 to produce the magnetic field gradients $G_x$, $G_y$ and $G_z$ used for position encoding MR signals. The gradient coil assembly 28 forms part of a magnet assembly 30 that includes a polarizing magnet 32 and a whole-body RF coil 34.

RF excitation waveforms are applied to the RF coil 34 by the RF system 26 to perform the prescribed magnetic resonance pulse sequence. Responsive MR signals detected by the RF coil 34 or a separate local coil (not shown in FIG. 1) are received by the RF system 26, amplified, demodulated, filtered, and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays (not shown in FIG. 1).

The RF system 26 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2},$$

and the phase of the received MR signal may also be determined:

$$\phi=\tan^{-1}Q/I.$$

The pulse sequence server 18 also optionally receives subject data from a physiological acquisition controller 36. The controller 36 receives signals from a number of different sensors connected to the subject, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 that receives signals from various sensors associated with the condition of the subject and the magnet system. It is also through the scan room interface circuit 38 that a subject positioning system 40 receives commands to move the subject to desired positions during the scan.

The digitized MR signal samples produced by the RF system 26 are received by the data acquisition server 20. The data acquisition server 20 operates in response to instructions downloaded from the workstation 10 to receive the real-time MR data and provide buffer storage such that no data is lost by data overrun. In some scans the data acquisition server 20 does little more than pass the acquired MR data to the data processor server 22. However, in scans that require information derived from acquired MR data to control the further performance of the scan, the data acquisition server 20 is programmed to produce such information and convey it to the pulse sequence server 18. For example, during prescans, MR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process MR signals used to detect the arrival of contrast agent in an magnetic resonance angiography (MRA) scan. In all these examples the data acquisition server 20 acquires MR data and processes it in real-time to produce information that is used to control the scan.

The data processing server 22 receives MR data from the data acquisition server 20 and processes it in accordance with instructions downloaded from the workstation 10. Such processing may include, for example, Fourier transformation of raw k-space MR data to produce two or three-dimensional images, the application of filters to a reconstructed image, the performance of a backprojection image reconstruction of acquired MR data, the calculation of functional MR images, the calculation of motion or flow images, and the like.

Images reconstructed by the data processing server 22 are conveyed back to the workstation 10 where they are stored. Real-time images are stored in a data base memory cache (not shown) from which they may be output to operator display 12 or a display 42 that is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Figure 2:
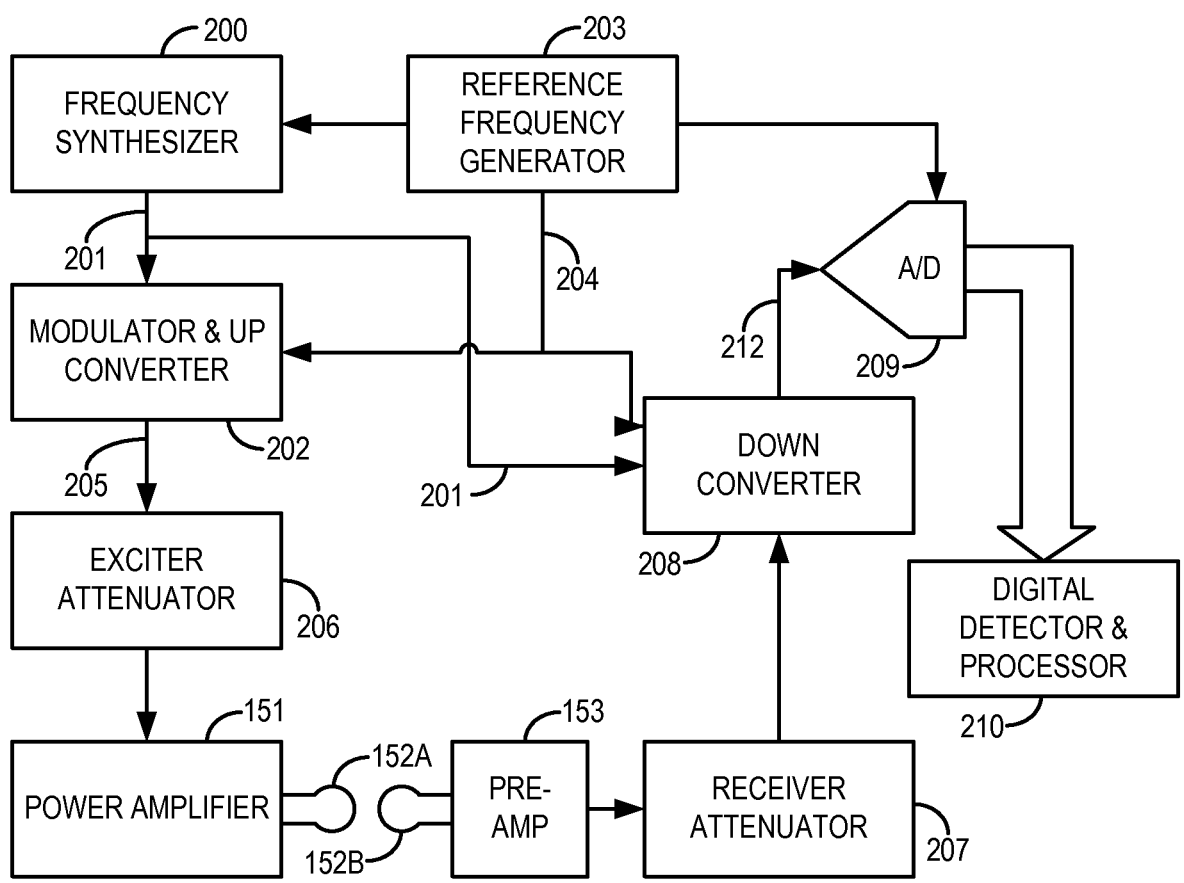
FIG. 2 is a block diagram of an RF system that forms part of the MRI system of FIG. 1.

As shown in FIG. 1, the RF system 26 may be connected to the whole body RF coil 34, or as shown in FIG. 2, a transmitter section of the RF system 26 may connect to one RF coil 152A and its receiver section may connect to a separate RF receive coil 152B. Often, the transmitter section is connected to the whole body RF coil 34 and each receiver section is connected to a separate local coil 152B.

Referring particularly to FIG. 2, the RF system 26 includes a transmitter that produces a prescribed RF excitation field. The base, or carrier, frequency of this RF excitation field is produced under control of a frequency synthesizer 200 that receives a set of digital signals from the pulse sequence server 18. These digital signals indicate the frequency and phase of the RF carrier signal produced at an output 201. The RF carrier is applied to a modulator and up converter 202 where its amplitude is modulated in response to a signal R(t) also received from the pulse sequence server 18. The signal R(t) defines the envelope of the RF excitation pulse to be produced and is produced by sequentially reading out a series of stored digital values. These stored digital values may be changed to enable any desired RF pulse envelope to be produced.

The magnitude of the RF excitation pulse produced at output 205 is attenuated by an exciter attenuator circuit 206 that receives a digital command from the pulse sequence server 18. The attenuated RF excitation pulses are applied to the power amplifier 151 that drives the RF coil 152A.

Referring still to FIG. 2, the signal produced by the subject is picked up by the receiver coil 152B and applied through a preamplifier 153 to the input of a receiver attenuator 207. The receiver attenuator 207 further amplifies the signal by an amount determined by a digital attenuation signal received from the pulse sequence server 18. The received signal is at or around the Larmor frequency, and this high frequency signal is down converted in a two step process by a down converter 208 that first mixes the MR signal with the carrier signal on line 201 and then mixes the resulting difference signal with a reference signal on line 204. The down converted MR signal is applied to the input of an analog-to-digital (A/D) converter 209 that samples and digitizes the analog signal and applies it to a digital detector and signal processor 210 that produces 16-bit in-phase (I) values and 16-bit quadrature (Q) values corresponding to the received signal. The resulting stream of digitized I and Q values of the received signal are output to the data acquisition server 20. The reference signal as well as the sampling signal applied to the ND converter 209 are produced by a reference frequency generator 203.

Subject Data Acquisition

Figure 3:
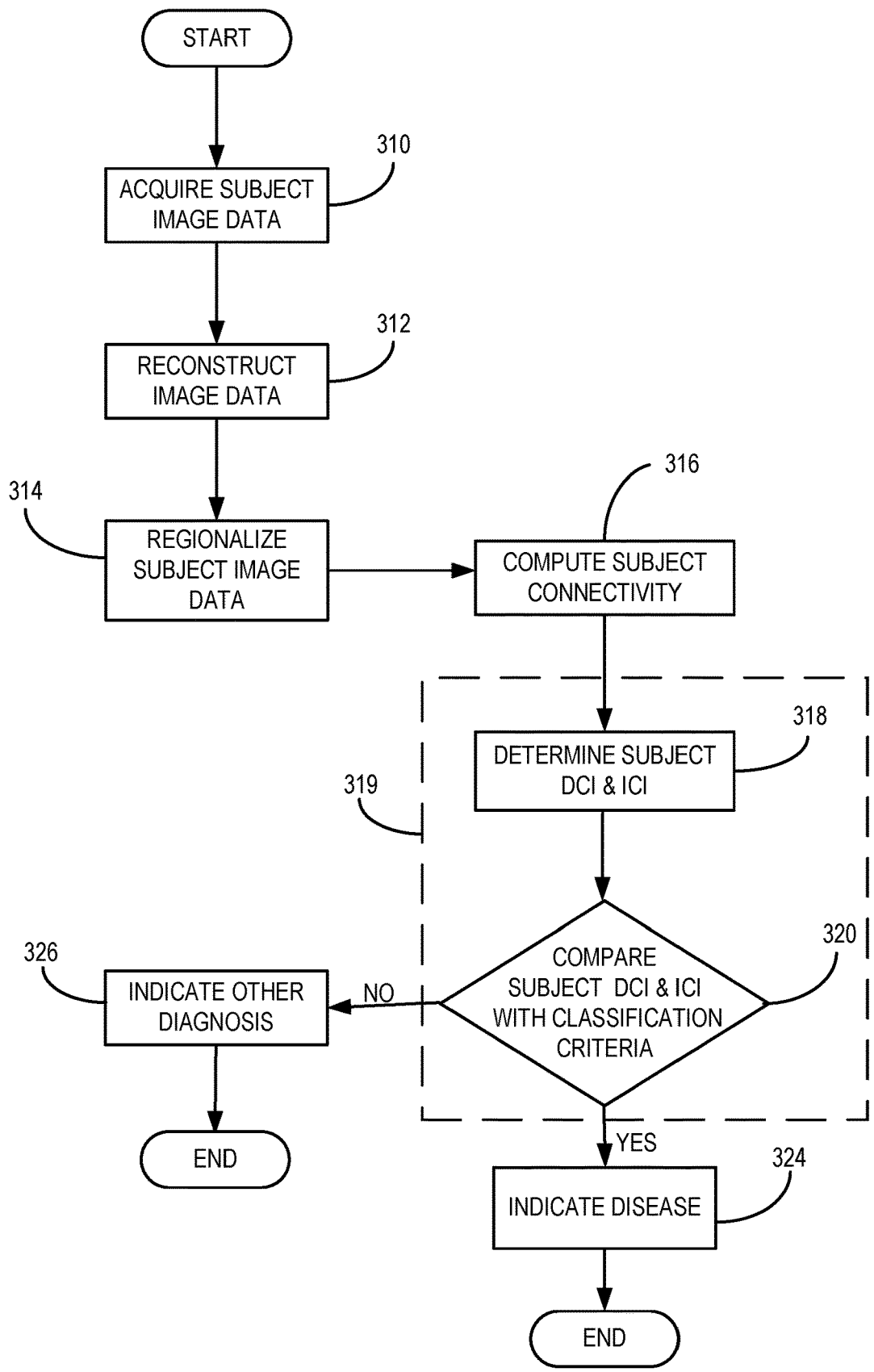
FIG. 3 a flow chart which illustrates the steps performed when practicing a preferred embodiment of the invention.

The data acquisition as described above and the processing of that data to produce a subject's connectivity data set, and determine changes in connectivity, such as a Decreased Connectivity Index (DCI), and an Increased Connectivity Index (IDI) that are used for classifying and quantifying the presence and the progress, or lack thereof, of a brain disease or disorder by measuring the functional connectivity changes in the whole human brain, may be performed under the direction of programs executed by the MRI system and/or other processor based systems. The steps performed while practicing a preferred embodiment of the invention are set forth in FIG. 3. Referring particularly to FIG. 3, the first step is to acquire functional image data from the subject's brain as indicated at process block 310.

To practice embodiments of the invention, imaging may be performed using a known MRI system, such as a whole-body 3T Signa GE scanner. A standard transmit receive head coil is used in place of the whole body RF coil to receive the MR signals produced in the brain. The imaging may be performed during a resting state, with no specific cognitive tasks being performed, and each subject may be instructed to close their eyes and relax inside the scanner. Sagittal resting-state functional MRI (fMRI) datasets of the whole brain are obtained in a predetermined amount of time, e.g., six minutes, or more or less, with a single-shot gradient echo-planar imaging (EPI) pulse sequence. Exemplary fMRI imaging parameters are: TE of 25 ms; TR of 2 s; flip angle of 90 degrees; obtain 36 slices without gap; slice thickness is 4 mm with a matrix size of 64×64; and field of view of 24×24 cm. High-resolution spoiled GRASS (SPGR) 3D axial images are acquired for anatomical reference. Exemplary parameters are: TE/TR/TI of 4/10/450 ms; flip angle of 12 degrees; number of slices of 144; slice thickness of 1 mm; and matrix size of 256×192.

To make sure that cardiac and respiratory frequencies do not account for any significant artifacts in the low-frequency spectrum, a pulse oxymeter and respiratory belt may be employed to measure these physiological noise sources, and are then further processed to minimize the potential aliasing effects.

Foam padding may be employed to limit head motion within the local head coil and then localized T1-weighted axial and sagittal plane slices are acquired to provide anatomic images which help define the number of slices and their location for the time course MR image data acquisition. The above-described EPI pulse sequence is then used as described above. The acquired images are reconstructed as indicated at process block 312 to form an image data set.

Figure 4:
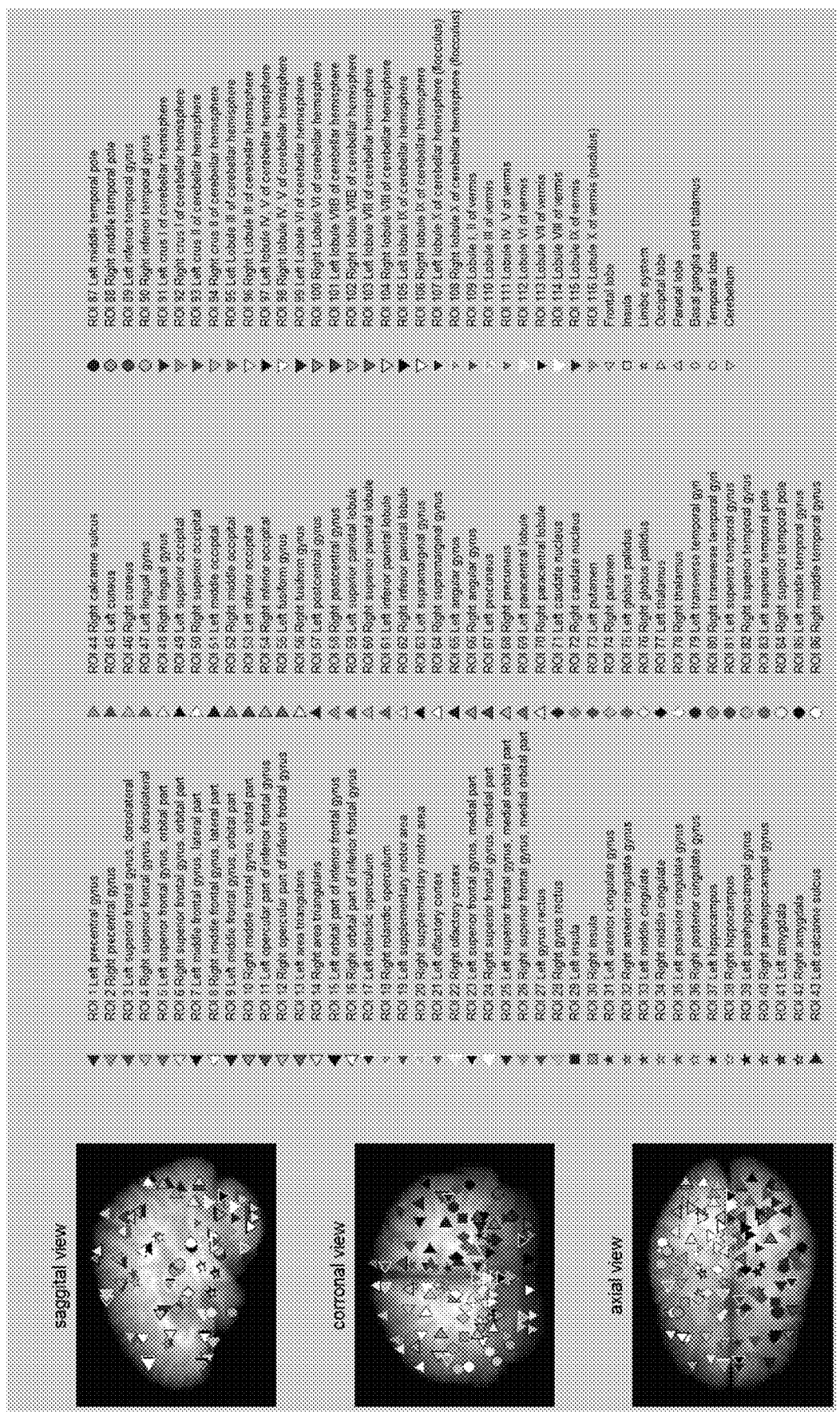
FIG. 4 is a pictorial representation of a template used in block 314 in the procedure of FIG. 3.

At process block 314, the subject's image data is regionalized into a number of regions of interest (ROI). In an exemplary embodiment shown in FIG. 4, a reference template in Talairach space, containing 116 anatomically defined ROIs is transformed and aligned to the image data set previously formed at process block 312 for each subject, which results in 116 mapped ROIs. FIG. 4 also includes the list and labeling of geometrical center locations of the 116 ROIs. Each ROI is identified by a unique combination of markers with shape, face color and edge color. The 116 ROIs may be divided into eight groups according to their anatomical regions and each group is marked with a unique shape (e.g., all the ROIs in the frontal lobe are marked by a triangle with one vertex pointing to the left). To uniquely label each ROI within a group, eight face colors (blue, green, red, cyan, magenta, yellow, black and white) and four edge colors (red, black, white and green) are employed. The ROI markers are labeled at the geometrical center of the ROIs on the projected images. It is to be appreciated that applying the concept of ROI in Talairach space in time-course functional-connectivity classification is considered a part of this invention described herein. It is also to be appreciated that the number of ROIs may be more or less than 116.

The average time course within each ROI may be extracted from the resting-state functional imaging data sets. Each of the 116 averaged time course data may then be preprocessed. A series of preprocessing steps that are common to most fMRI analyses may be conducted to obtain the averaged low-frequency BOLD signal time course for each region. The preprocessing may include allowing for T1-equilibration effects, slice-acquisition-dependent time shifts correction, despiking, motion correction, detrending, removal of cardiac, respiratory, white matter, cerebrospinal fluid (CSF) and global signal effect and low frequency band-pass filtering, as non-limiting examples. The cardiac aliasing may be minimized with the known RETROICOR program, and the respiratory volume variation may be minimized based on the respiratory belt signal. Possible white matter, CSF, and global signal contaminations may be removed using known linear regression. Finally, a band-pass filter may be applied to keep low-frequency fluctuations to within 0.015 Hz and 0.1 Hz. It is to be appreciated that subject data may also be utilized that has been acquired using other methods, such as those described in U.S. Pat. No. 7,577,472.

Functional Connectivity

The subject's regionalized data from process block 314 may then be assessed to create the subject's functional connectivity, or functional connectivity data set, as indicated at process block 316. In some embodiments, the functional connectivity between a set of ROIs, such as between any two brain regions (paired ROIs) may be assessed by the Pearson product-moment correlation coefficient (CC), although other assessment methods are contemplated. The CC values may be age corrected because age is a risk factor in AD. In the exemplary embodiment, there are 6,670 (116×115/2) pairwise CC values among the 116 ROIs for each subject. These CC values can then be arranged in functional connectivity data sets, which in some embodiments are shown as matrices, as shown in FIGS. 5A, 5B, and 5C.

Figure 5A:
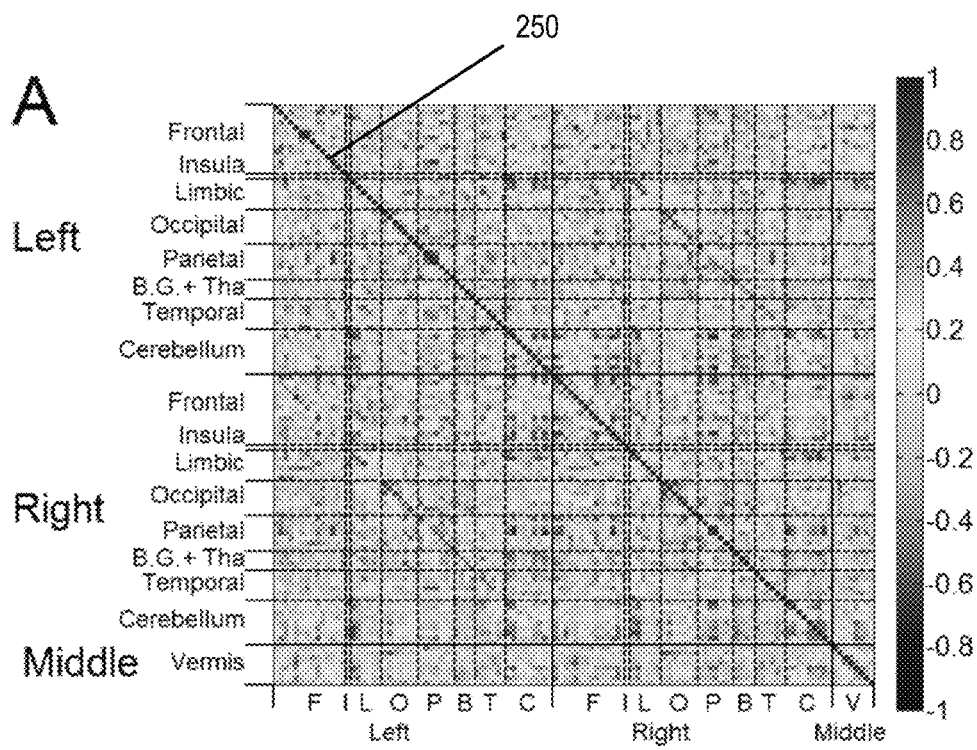
FIGS. 5A to 5D are graphic representations of functional connectivity data sets generated in block 316 as indicated in FIG. 3.
Figure 5B:
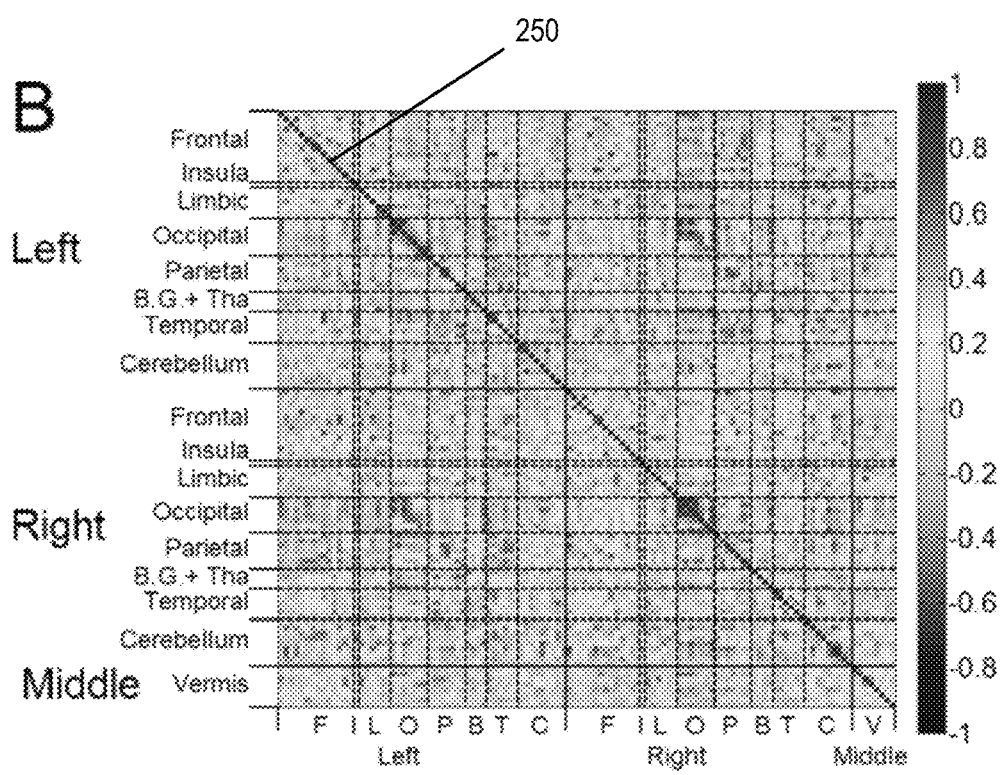
Figure 5C:
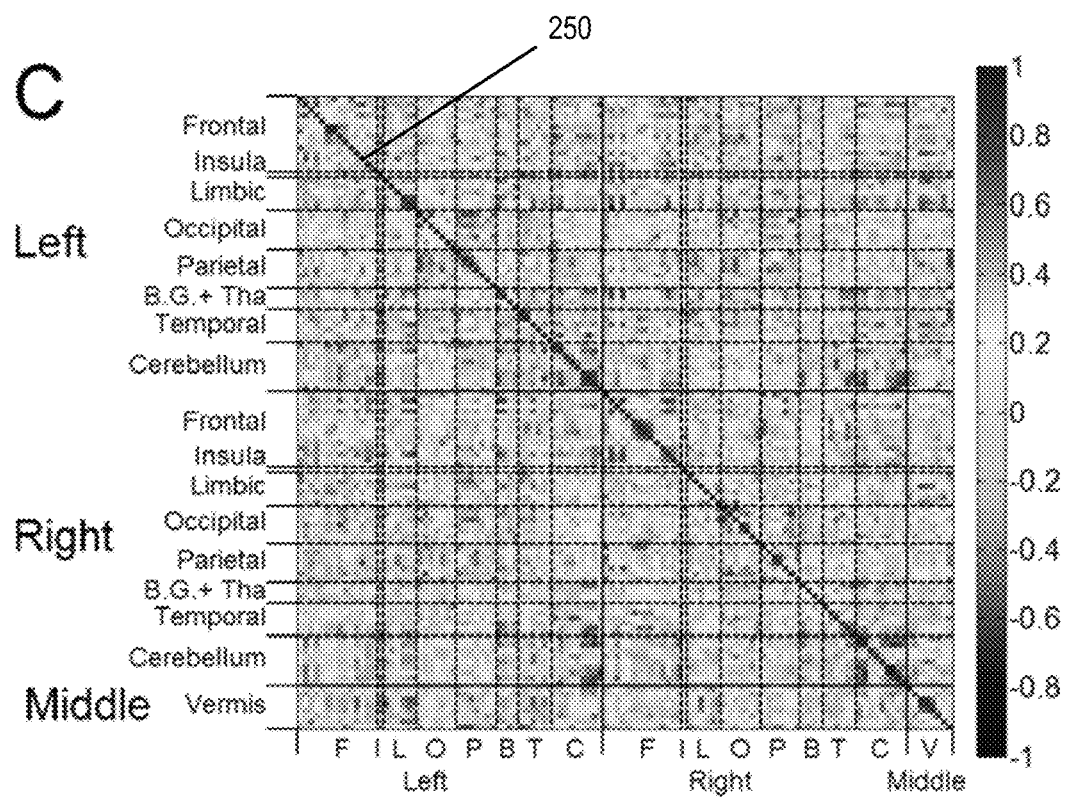

FIG. 5A shows an exemplary functional connectivity matrix from a representative CN patient, FIG. 5B shows an exemplary functional connectivity matrix from a representative AD subject, and FIG. 5C shows an exemplary functional connectivity matrix from a representative aMCI subject. In each of the connectivity matrices, the upper right 6670 CC values are always symmetrical to the lower left 6670 values along the diagonal 250. The bars on the right show the CC values. Each subject has such a functional connectivity matrix. Although the term of functional connectivity matrix is used herein, it is to be appreciated that one embodiment of the invention is to measure only selected elements of the functional connectivity matrix (representing selected paired ROIs) that are important to a given classification application.

Classification Methodology

Several aspects of this invention related to classification methodology are described below.

Increase and Decrease of Functional Connectivity

Considering both the decrease and the increase of the functional connectivity in classification (i.e., 2-dimensional classification, as to be discussed below and in regards to FIG. 11) is to be considered a part of this invention. The previous 1-dimensional classifications are also to be considered one embodiment of the invention.

DCI & ICI

The general terms Decreased Connectivity Index (DCI) and Increased Connectivity Index (ICI) are used herein to capture the change (decrease and increase) of the functional connectivity of a subject. In general, DCI can be any linear or non-linear function of the subject's assessed regionalized data, such as the CC values at selected elements of the functional connectivity matrix. Similarly, ICI can be any linear or non-linear function of the subject's assessed regionalized data, such as the CC values at selected elements of the functional connectivity matrix.

In one embodiment, the function mentioned above can be a simple averaging over selected elements of the functional connectivity matrix. By calculating the DCI and ICI indices for each subject, the 6,670 CC values per subject can be reduced to a more manageable two values per subject.

The next step in the process is to determine any linear or non-linear function of identifiable decreased connectivity and/or any linear or non-linear function of identifiable increased connectivity. The decreased connectivity and/or increased connectivity may range from identifiable connectivity changes to significant connectivity changes. In one exemplary embodiment, and as indicated at process block 318 in FIG. 3, the process may include determining the subject's Decreased Connectivity Index (DCI) and Increased Connectivity Index (ICI) accordingly.

Decreased Connection Set and Increased Connection Set

The selected elements over which a DCI is evaluated are called the decreased connection set, representing important paired-ROIs where a decreased connection should be checked for a specific classification application. Similarly, the selected elements over which an ICI is evaluated are called the increased connection set, representing important paired-ROIs where an increased connection should be checked for a specific classification task.

The decreased connection set and the increased connection set are typically derived a priori using pattern recognition methods based on some a priori knowledge. As one example, they can be derived by comparing the corresponding changes between different classes (may also be referred to as groups) in training data, where the knowledge of which subject in the training data belongs to which class is known. One embodiment of deriving the decreased connection set and the increased connection set is by statistical hypothesis testing between different classes to find the combination of the decreased connection set and the increased connection set that gives best classification performance, as described in an example below.

Classification Algorithm (Criteria)

In the classification step, as shown at process block 320 in FIG. 3, the subject specific information, including the DCI and ICI, may be used in a classification algorithm (criteria) for determining whether the subject should be classified as a certain class. Based on the classification, an indication of disease (at process block 324) or other diagnosis (at process block 326) may be given.

The classification algorithm (criteria) are typically derived using pattern recognition methods based on some a priori knowledge. As previously described, in one example, the classification algorithm can be derived by comparing the corresponding functional connectivity between different classes in training data, where the knowledge of which subject in training data belongs to which class is known. One embodiment of deriving the classification algorithm (criteria) is to use Fisher linear discriminant analysis between different classes.

Classifiers

DCI, ICI, the decreased connection set, the increased connection set, and the classification algorithm (criteria) are, collectively, called a classifier, noted as process block 319 in FIG. 3. The classifier typically includes both an increased functional connectivity within the regions of interest and a decreased connectivity within the regions of interest. As described above, the classifier may be derived by detecting corresponding differences between different classes in the training data and validated using a validation cohort.

Optimizing Classification Performance Using ROC

One commonly used metric for evaluating the accuracy of a classifier is the receiver operating characteristic (ROC) curve and the area under the ROC curve (AUC). By optimizing ROC performance, the decreased connection set, the increased connection set, and other empirical parameters can be determined.

Multi-Step Classification For Three Or More Classes

Figure 8:
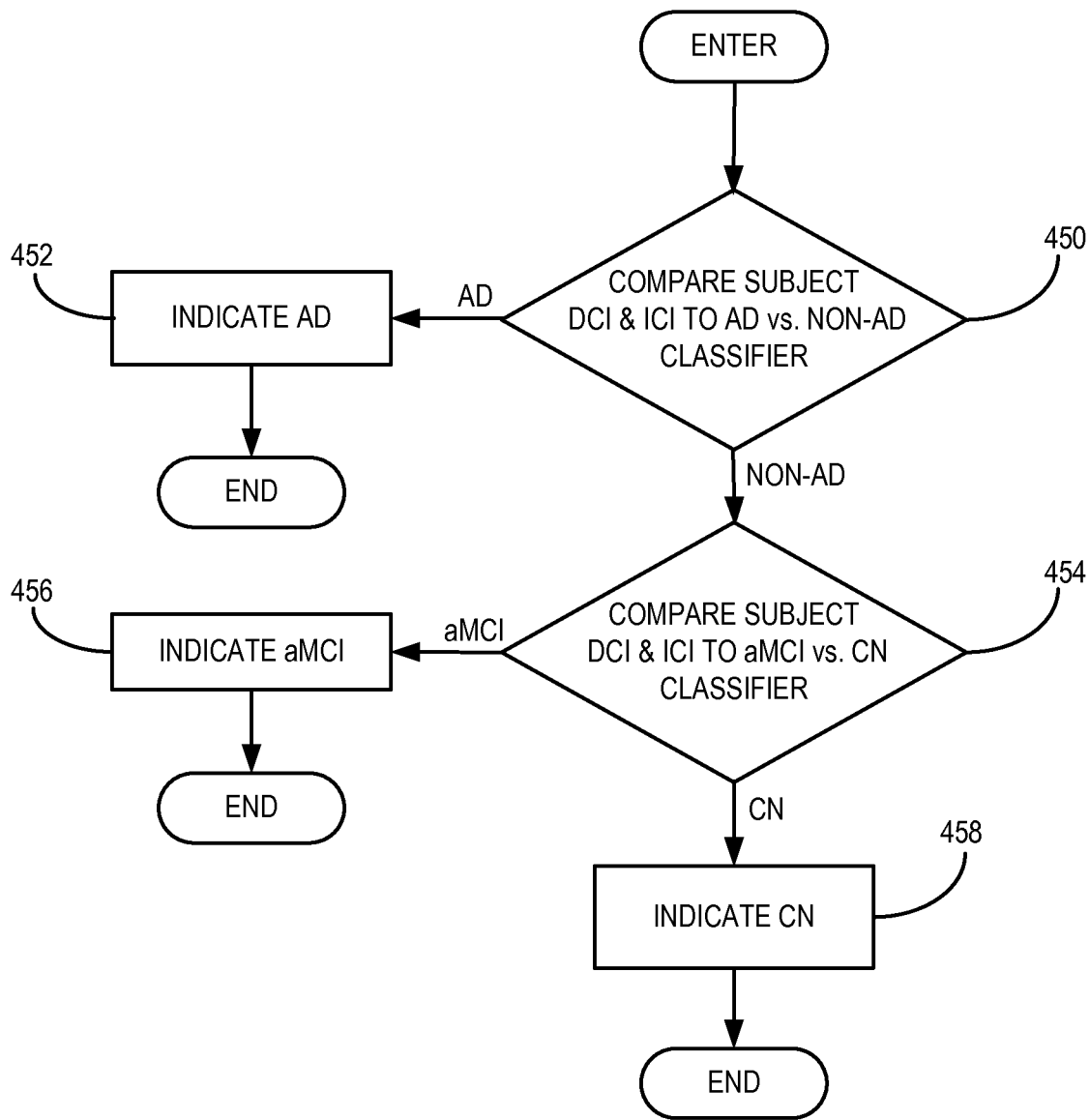
FIG. 8 is an embodiment of a flow chart of steps performed in block 319 as indicated in FIG. 3.

The classifier shown at process block 319 can be further refined to a multi-step approach. FIG. 8 shows a two-step classification that may be incorporated into the steps of the present invention (e.g., a tri-group classification scenario), where in the first step, AD subjects are discriminated from non-AD subjects (the non-AD group contains aMCI and CN subjects), and in the second step, aMCI subjects are discriminated from the CN subjects based on the results obtained from the first step.

In the first step shown at decision block 450, which is similar to process block 319, the subject's DCI and ICI are compared to the AD vs. non-AD classifier. If an indication of AD is given (process block 452), the process may end here. If an indication of non-AD is given, the second step shown at decision block 454 may be performed, where the subject's DCI and ICI are further compared to the aMCI vs. CN classifier. Based on the comparison at decision block 454, an indication of aMCI is given (at process block 456), or an indication of CN is given (at process block 458).

Classifying AD, aMCI, and CN Using the Above Classification Methodology

As previously described, by thresholding, a set of negative CC values among all 6,670 possible pairwise CC values may be defined as the decreased connection set, and similarly, a set of positive CC values among all 6,670 possible pairwise CC values may be defined as the increased connection set. The averaged CC value in the decreased connection set for each subject is then defined as the Decreased Connectivity Index (DCI). Similarly, the averaged CC value in the increased connection set is defined as the Increased Connectivity Index (ICI).

Figure 5D:
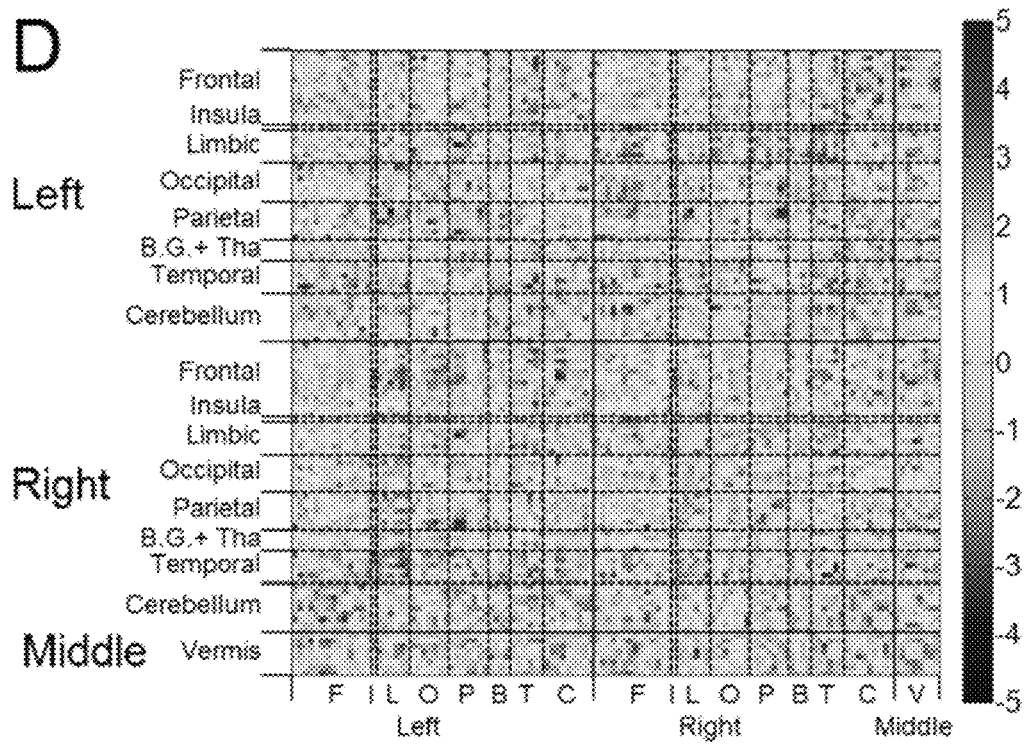
Figure 6:
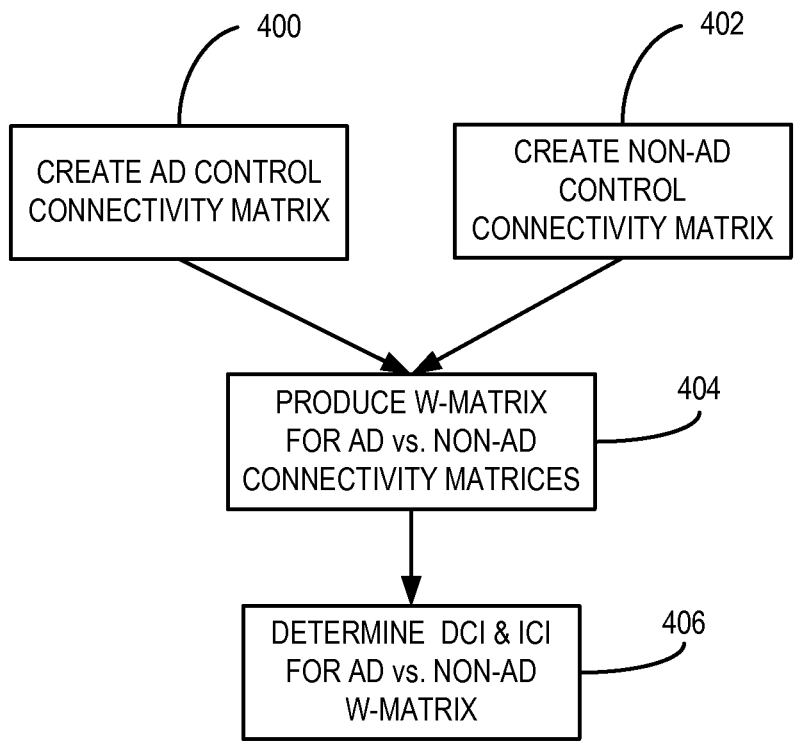
FIGS. 6 and 7 are flow charts which illustrate steps performed in a preferred embodiment of deriving classifiers.
Figure 10A:
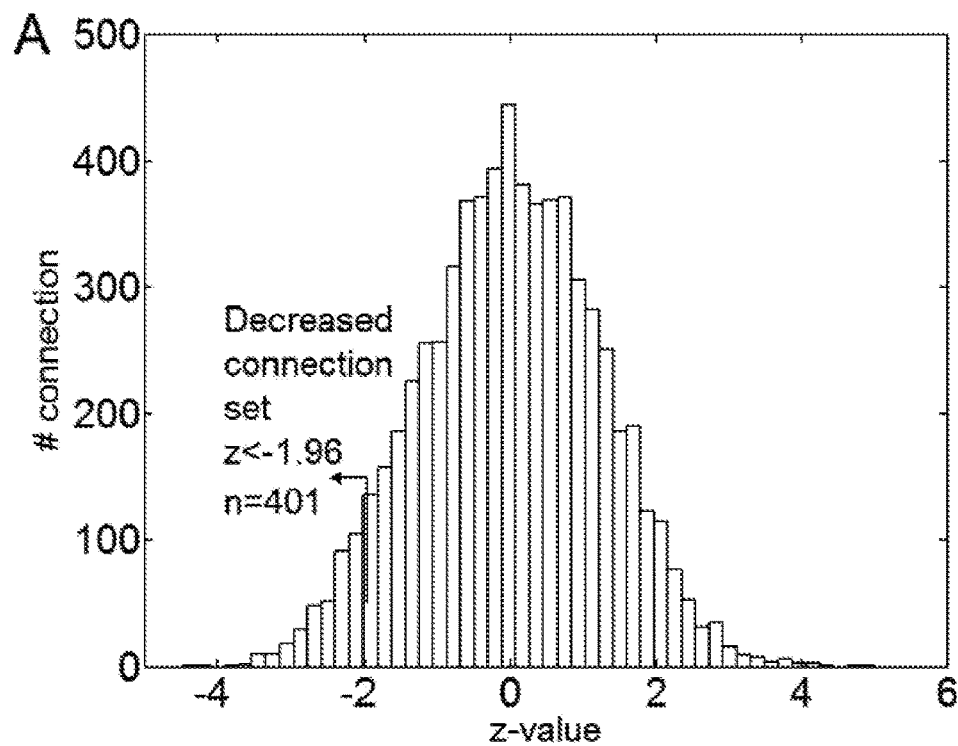
FIGS. 10A and 10B are graphical representations of intermediate results used for classifier derivation.

In an exemplary embodiment of the invention, the training data can include an AD group and a non-AD group. As shown in FIG. 6, an AD group functional connectivity matrix is generated at process block 400, and at process block 402, a non-AD group functional connectivity matrix is generated. At process block 404, statistical test(s) are performed to test for differences between the AD and non-AD groups. For this exemplary embodiment of the invention, the nonparametric two-sample Wilcoxon rank-sum test may be employed to compare the corresponding CC value distributions for each pair of ROIs between the AD vs. non-AD control groups. The reason for employing the nonparametric two-sample Wilcoxon rank-sum test instead of parametric tests (such as the t-test) is to avoid making any assumption about the distribution of the CC values. The Wilcoxon rank-sum test produces a matrix with 6,670 z-values, one for each pair of ROIs as shown in the AD vs. non-AD W-matrix at FIG. 5D. In the AD vs. non-AD W-matrix, the upper right 6670 z-values are symmetrical to the lower left 6670 values with respect to the main diagonal, similar to the CC matrices shown in FIGS. 5A to 5C. In FIG. 5D, the bar on the right shows the z-values. The absolute z-value indicates the statistical significance, while the sign of the z-value indicates which group has the higher mean CC value. The 6,670 pairwised z-values in the W-matrix were sorted, as shown in FIG. 10A. Again, by thresholding, as previously described, the DCI and ICI are determined for the AD vs. non-AD control groups at process block 406.

The comparison step is based on the discovery that different combinations of thresholding percentages varying from, e.g., 10% (667 connections) to 0.03% (2 connections) with the highest positive z-values or highest negative z-values may be chosen to empirically find out the best classification between two groups of training data. The thresholding of z-values for increased and decreased connectivity sets may be empirically determined.

Figure 7:
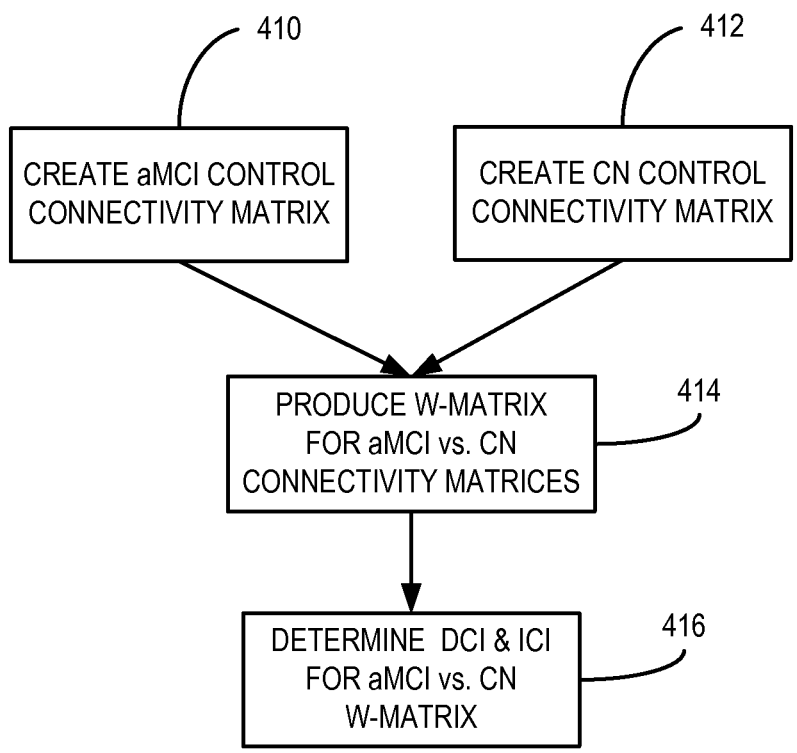

FIG. 7 shows similar steps as shown in FIG. 6, except they use the aMCI and CN groups. An aMCI group functional connectivity matrix is generated at process block 410, and at process block 412, a CN group functional connectivity matrix is generated. At process block 414, statistical test(s) are performed to test for differences beween the aMCI and CN groups. Some embodiments use the nonparametric two-sample Wilcoxon rank-sum test to compare the corresponding CC value distributions for each pair of ROIs between the aMCI vs. CN control groups. The DCI and ICI are determined for the aMCI vs. CN groups at process block 416.

To evaluate the accuracy of the classification using DCI and ICI, the "resubstitution method" error estimate may be employed. Note that in the resubstitution method, the same subjects are used for both training and evaluation, otherwise the method may give an overly optimistic estimate. Alternatively, the Leave-One-Out (LOO), or in general, leave N out, error estimate method can be employed in order to make up for the lack of independence between the training and testing sets in the resubstitution method. The LOO method uses one subject at a time for evaluation, with the remaining subjects being used for training. That is, the classification criteria are determined using all subjects except the one subject to be evaluated. This entire process may be repeated for each subject in the selected control group, thereby providing an unbiased estimate of a classification error rate.

In the first step of one study, 55 LOO processes were performed. For example AD subject No. 1 was left out in the first LOO process. A W-matrix was produced between the AD group consisting of the rest of the 19 AD subjects and the non-AD group of 35 subjects. The 6,670 pairwised z-values in the W-matrix were sorted, as shown in FIG. 10A. Then, a number of connections with the largest negative z-values was defined as the decreased connection set. The averaged CC value in the decreased connection set for each subject was obtained as the Decreased Connectivity Index (DCI). Similarly, a number of connections with the largest positive z-values were defined as the increased connection set, and the averaged CC value in the increased connection set as the Increased Connectivity Index (ICI). However, the numbers of decreased and increased connections that could classify the AD and non-AD group were not known a priori, and could affect the classification. To optimize classification accuracy, different combinations of decreased and increased connections were evaluated for their classification performances (see the chart shown in FIG. 17 for the list of combinations). Fisher's linear discriminant analysis was performed with the DCI and ICI to classify a subject as either AD or non-AD, using the MatLab "classify" function (Mathworks,Natick, Mass.). The process was repeated 55 times with different LOO subjects. As previously described, one commonly used metric for evaluating the accuracy of a classifier is the receiver operating characteristic (ROC) curve and the area under ROC curve (AUC). In order to obtain the ROC curve, different weights were assigned to the sensitivity and specificity in the classify function, the LOO analysis was repeated with 1,001 different weights in order to obtain a reasonably smooth ROC curve.

There were 484 combinations with the highest AUC of 0.93. Considering that AD could cause a large amount of large scale network (LSN) connection dysfunctions instead of a limited amount in a few connections, individual connections with a threshold of $z<-1.96$ (uncorrected for multiple comparisons) were employed in the study to classify AD from non-AD subjects, as shown in FIG. 10A. For the theoretical, continuous normal distribution, a z-value of 1.96 is associated with a two-sided p-value of 0.05. Considering those increased connection sets (i.e., connections with positive z-values where connections in the AD group were stronger than those in the non-AD group) may be related to compensatory effects and may decrease with the disease progression, the increased connection set was not employed. The Fisher's linear discriminant analysis with LOO cross-validation was performed with the DCI to classify the 55 subjects as either AD or non-AD. The ROC curve was obtained in the same fashion, as described above.

Figure 10B:
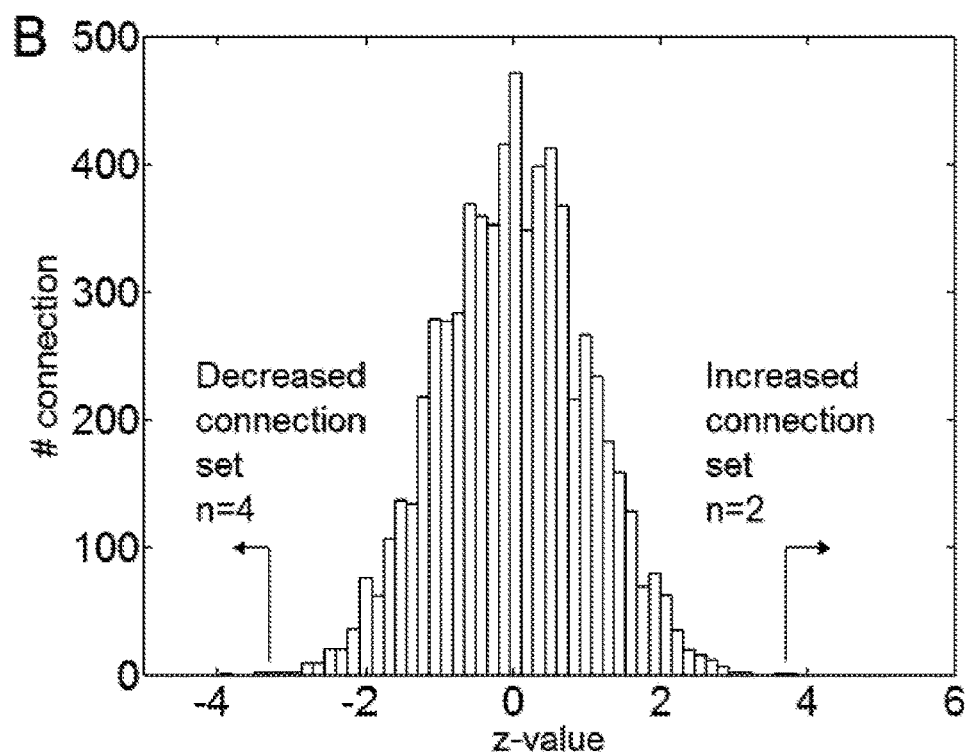

Similarly, in the second step, 35 LOO processes were performed between the CN and aMCI groups. In this step, 361 different combinations of decreased and increased connections were evaluated for their classification performance (see the chart shown in FIG. 18 for the list of combinations). For generating the ROC curve between aMCI and CN classification, a similar method was conducted as described above. The highest AUC occurred at one decreased connection combined with two increased connections (AUC 0.96). Because only one decreased connection may be undertraining the classifier, a set of four decreased connections with a set of two increased connections were employed (AUC 0.95), as shown in FIG. 10B. For those AD subjects that were classified as non-AD subjects in the first step classification, the same classifier (the set with four decreased connections and two increased connections) was applied to classify them as either aMCI or CN subjects.

Results

As described above, each subject has a functional connectivity matrix. FIG. 5A shows a representative functional connectivity matrix of a CN subject. FIG. 5B shows a representative functional connectivity matrix of an AD subject, and FIG. 5C shows a representative functional connectivity matrix of an aMCI subject. In comparing control group differences in functional connectivity in all of the pairwised ROIs, a W-matrix can be obtained. FIG. 5D illustrates the W-matrix when the AD group and the non-AD group are compared.

Figure 9A:
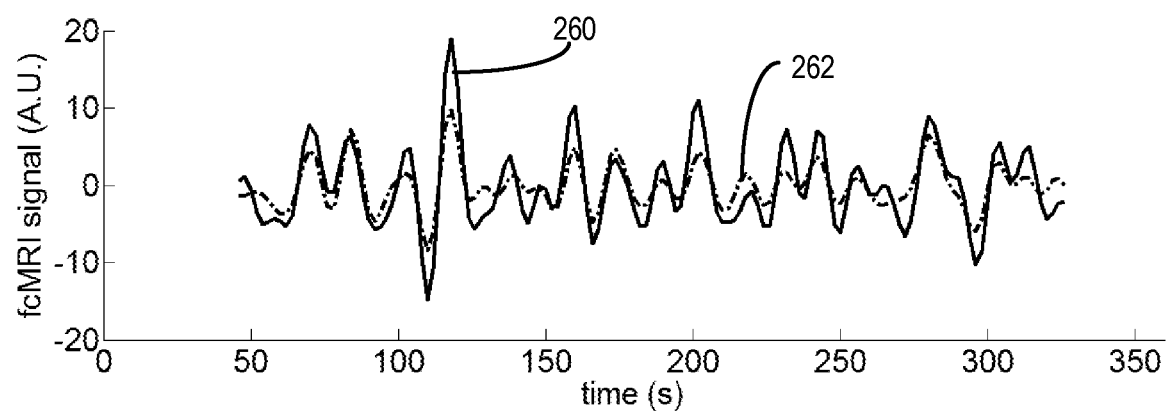
FIGS. 9A and 9B are graphical representations of a cross-correlation between representative regions of interest (ROIs)
Figure 9B:
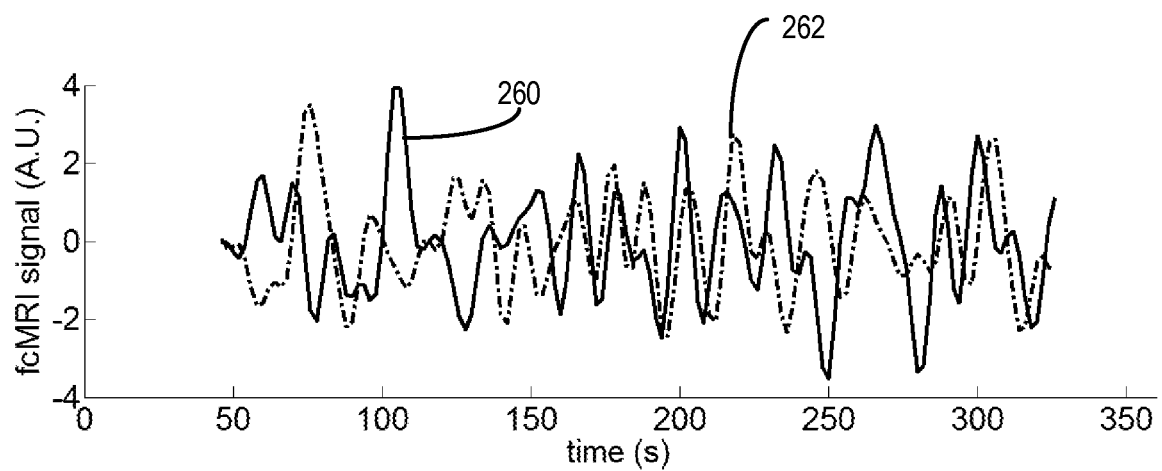

FIGS. 9A and 9B show a representative cross-correlation between ROI 84 (right superior temporal pole) solid line 260 and ROI 88 (right middle temporal pole) dash-dotted line 262. The preprocessed time courses extracted from ROI 84 and ROI 88 are strongly correlated (CC=0.90) in a CN subject (see FIG. 9A), but not in an AD subject (CC=-0.02) (see FIG. 9B). The z-value for the pair (ROI 84 and ROI 88) between the AD group and the non-AD group is -3.51, demonstrating weaker functional connectivity between the two ROIs in the AD group.

Figure 12:
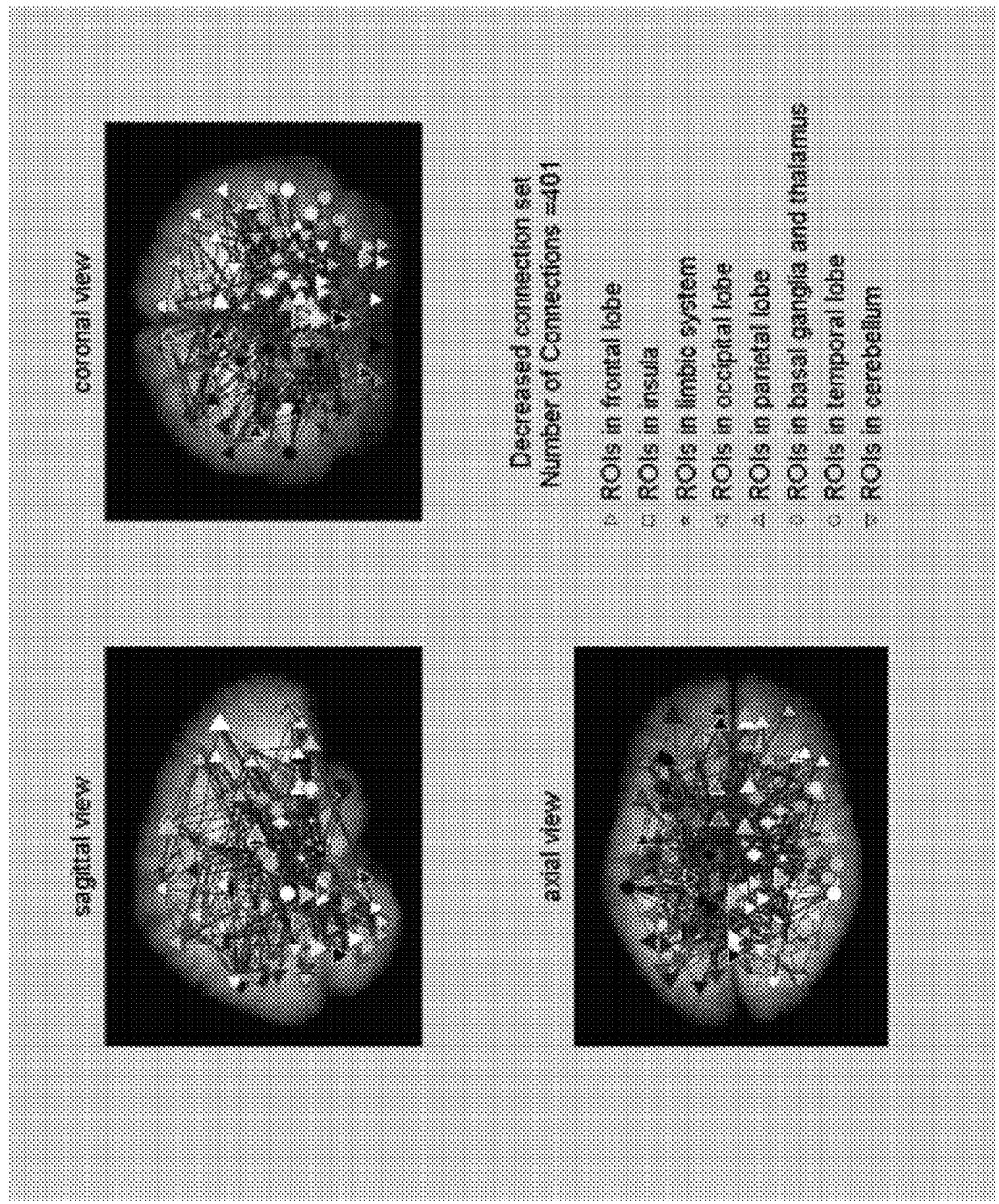
FIGS. 12 to 13B are pictorial representations of classification results.

FIG. 10A shows the distribution of z-values in the W-matrix between AD and non-AD groups. In the AD and non-AD classification, it was discovered that the classifier for AD vs. non-AD was thresholded as $z<-1.96$. These results are visually displayed in FIG. 12 using the reference template in Talairach space.

Figure 13A:
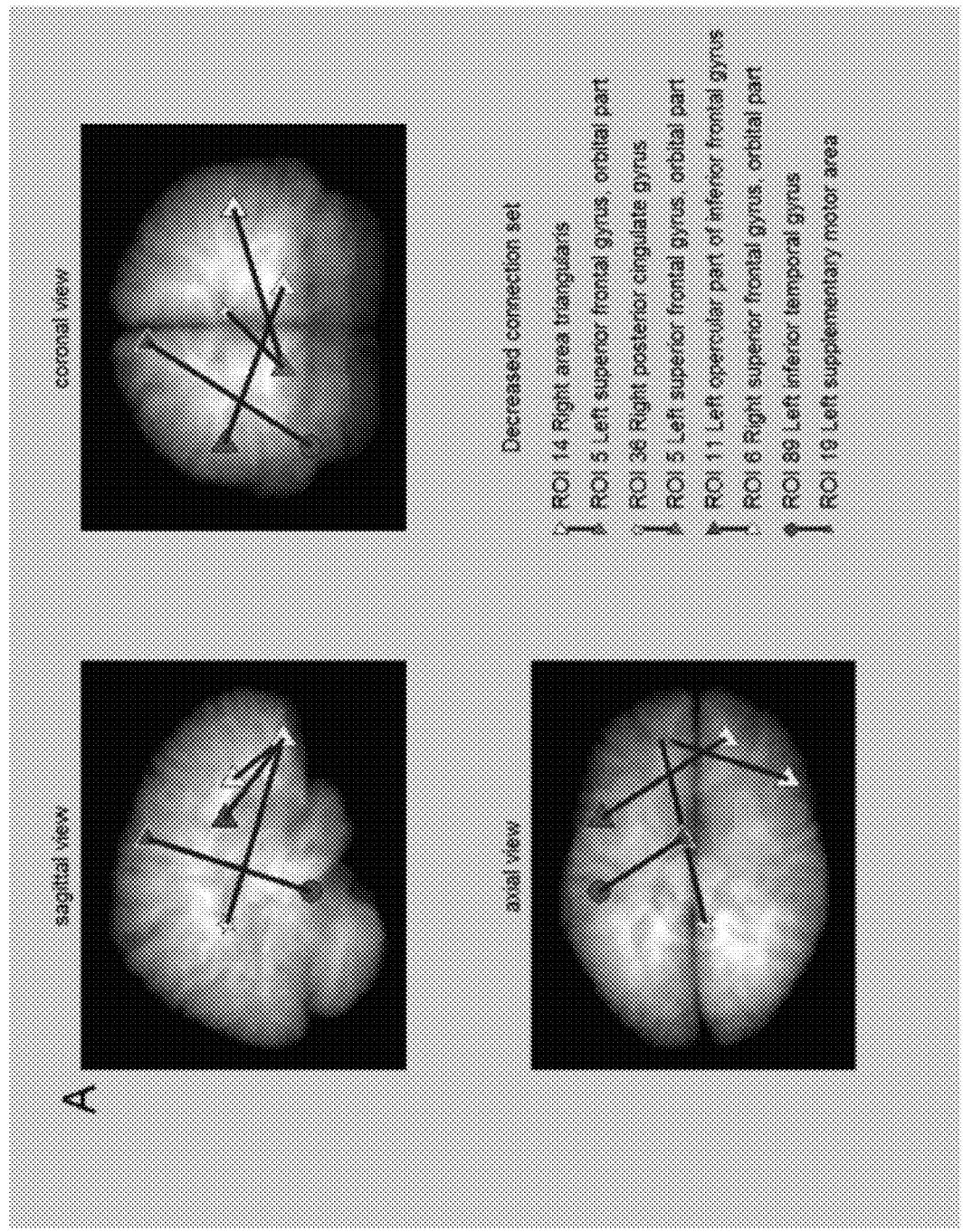
Figure 13B:
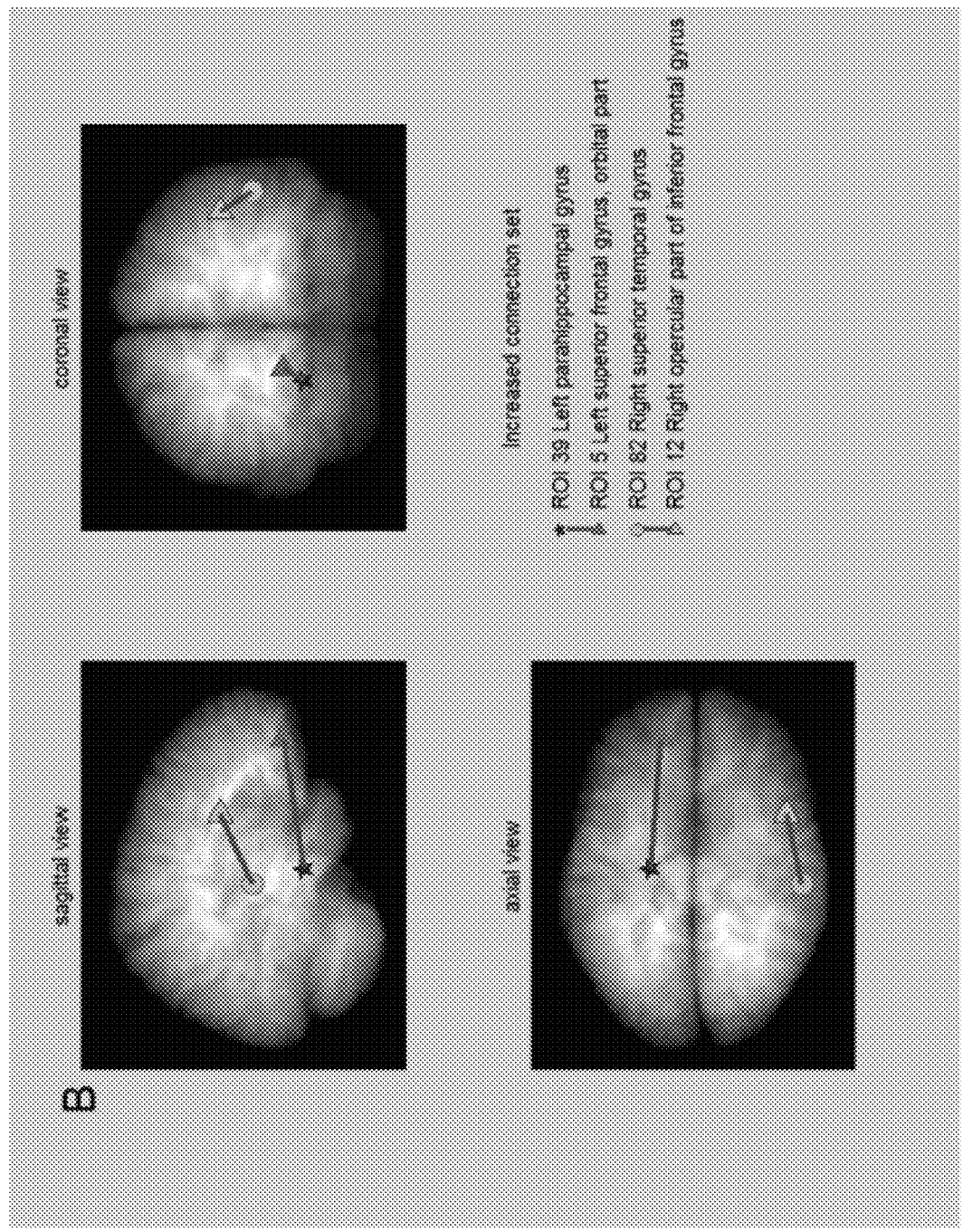

Similarly, FIG. 10B shows the distribution of z-values in the W-matrix between aMCI and CN groups. In the aMCI and CN classification, it was discovered that the classifier for aMCI vs. CN was a combination of four decreased connections and two increased connections. Again, these results are visually displayed in FIG. 13A (four decreased connections) and FIG. 13B (two increased connections) using the reference template in Talairach space.

Figure 11:
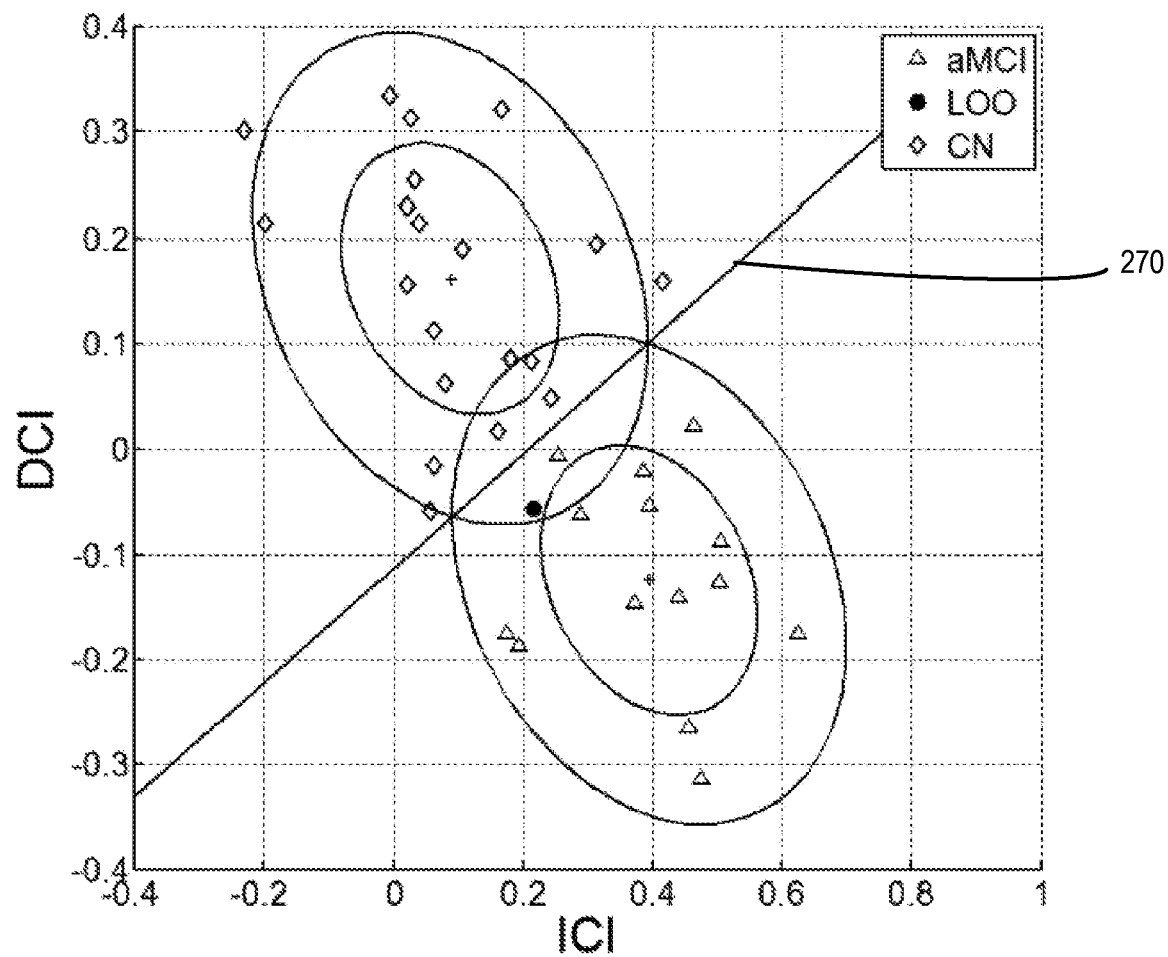
FIG. 11 is a graphical representation of classification.

FIG. 11 shows a representative result of the LOO cross-validation method between aMCI and CN subjects. In the LOO procedure, one aMCI subject was left out (labeled with a filled circle) and the other 14 aMCI subjects (labeled with triangles) and 20 CN subjects (labeled with diamonds) are used for establishing classification criteria using a multi-variate classification algorithm. A preferred embodiment uses the Fisher linear discriminant analysis. That is, the classification criteria are determined using all subjects except the one subject to be evaluated. As a result of the Fisher linear discriminant analysis, the aMCI subject that was left out in the beginning was correctly classified as an aMCI subject (i.e., the filled circle appears below the straight line discriminant boundary 270). The ellipses represented the 50% and 90% probability containment for the aMCI and CN groups, respectively. Clearly, the clinically defined aMCI subject is correctly classified with the altered functional connectivity in the large-scale network (LSN). This LOO procedure may be carried out once for each subject.

FIGS. 14A through 14D summarizes the overall classification results. FIG. 14A shows the results of the first step: classify AD subjects from non-AD subjects. Among the clinically defined 20 AD and 35 non-AD subjects, the LSN classifier provided 85% sensitivity and 80% specificity, 20% false positive and 15% false negative rates with an accuracy of 81.8%. FIG. 14B shows the results of the second step: classify aMCI subjects from CN subjects among the 35 subjects. Among these 35 subjects, in the second step, the large LSN classifier provided 93% sensitivity and 90% specificity, 10% false positive and 7% false negative rates with an accuracy of 91.4%. For the three clinically defined AD subjects that were classified as non-AD subjects, two were classified as aMCI and one as a CN subject. Taking a closer look, among the 14 aMCI subjects, three were classified as AD in the first step; among the 18 CN subjects, three were classified as AD subjects. There were two CN subjects that were classified as aMCI subjects; one of the two was an AD subject from the first step.

By combining the results from the first and second steps, as shown in FIG. 14C, among the 20 clinically defined AD subjects, 17 AD subjects were confirmed, two were classified as aMCI and one was ruled out as a CN subject; among the 15 aMCI subjects, 11 were confirmed, three were classified as AD, and one was a CN subject; for the 20 CN subjects, 15 were confirmed, four were classified as AD and one was an aMCI. In noting that aMCI subjects have a great risk to convert to AD and are defined as the diseased category with the AD group, FIG. 14D shows the overall classification results: among the 35 clinically defined diseased subjects (20 AD and 15 aMCI), 33 (94%) were confirmed and two (6%) were false negative; for the 20 CN subjects, 15 (75%) were confirmed and five (25%) were false positive.

Figure 15A:
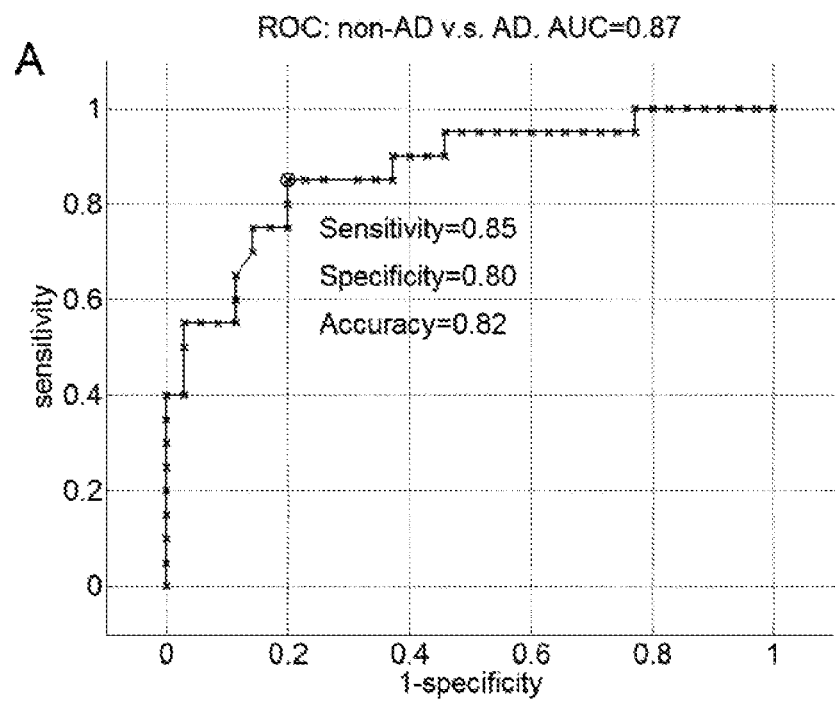
FIGS. 15A to 16B are graphical representations that show the classifier performance and cross-validation.
Figure 15B:
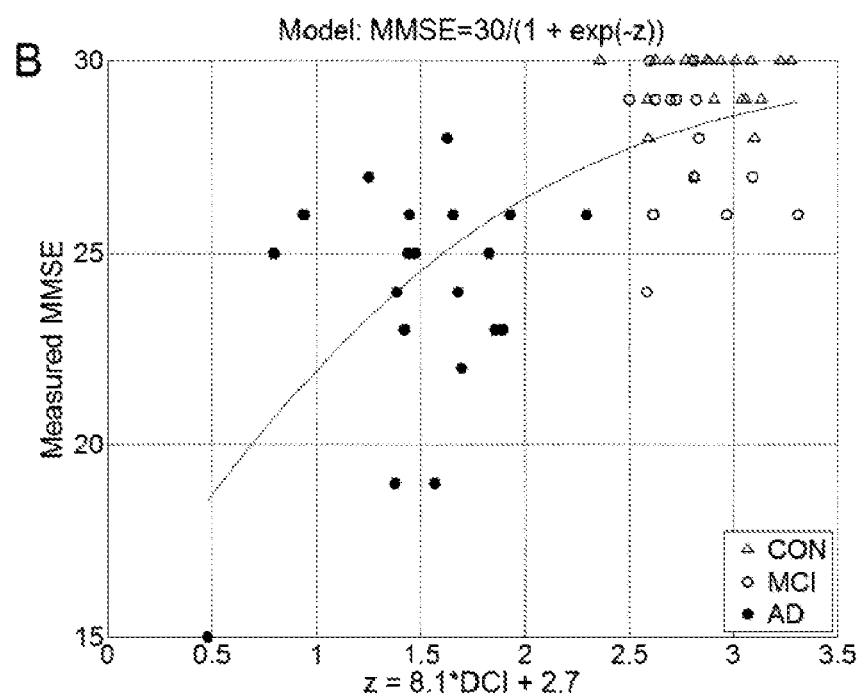
Figure 16A:
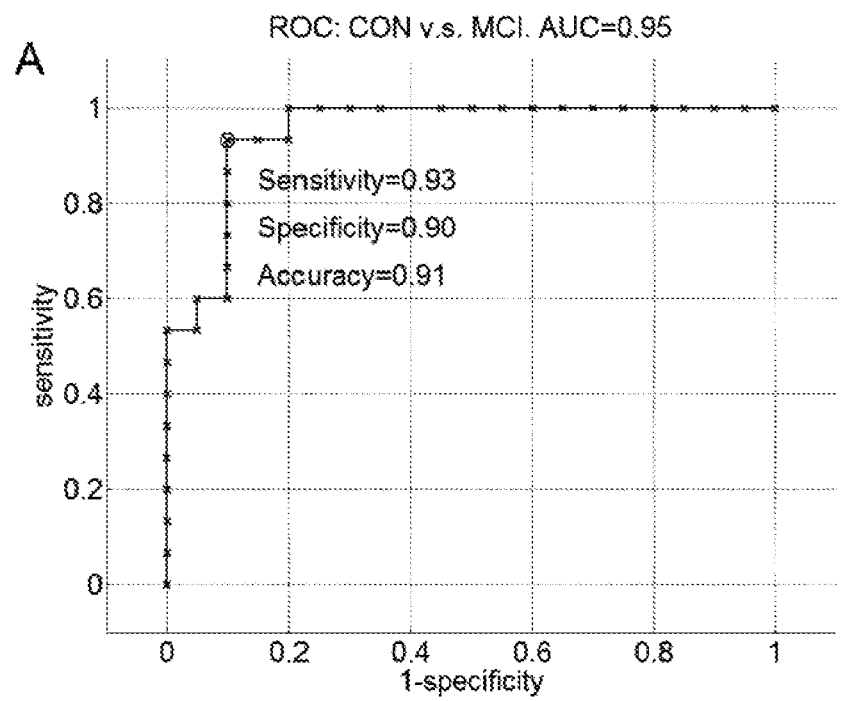
Figure 16B:
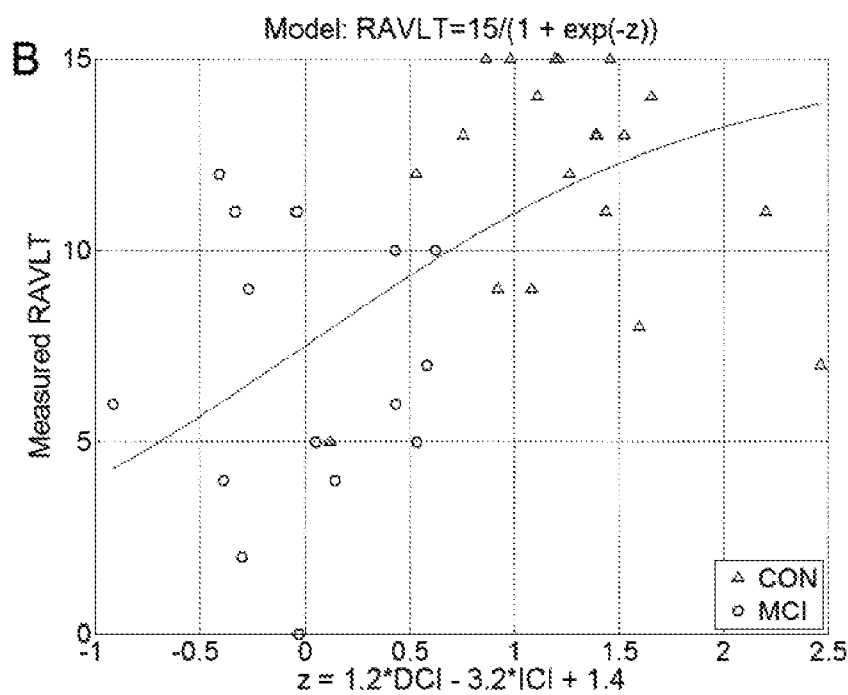

As previously discussed, one commonly used metric for evaluating the accuracy of a classifier is the receiver operating characteristic (ROC) curve and the area under ROC curve (AUC). In order to obtain the ROC curve, different weights may be assigned to the sensitivity and specificity in the classify function, and the LOO analysis was repeated with 1,001 different weights in order to obtain a reasonably smooth ROC curve. FIGS. 15A and 16A show the ROC curves, which demonstrate the distributions of the sensitivity and specificity of the LSN method. The ROC curve of FIG. 15A showed that the LSN method provided accurate classification between AD and non-AD subjects (AUC 0.87). At a sensitivity of 0.85, a specificity of 0.8, the accuracy is 0.82. The ROC curve of FIG. 16A showed that the LSN method provided accurate classification between aMCI and CN subjects (AUC 0.95). At a sensitivity of 0.93, a specificity of 0.90, the accuracy is 0.91. In investigating if the measured DCI and ICI indices correlate with behavioral scores, FIG. 15B shows that the DCI index significantly correlated with the Mini-Mental Status Examination (MMSE) scores. For example, FIG. 15B shows the relationship between MMSE scores and the decreased connectivity index (DCI), where (MMSE=30/(1+exp(-8.1DCI-2.7)); F=61.26; df=1, 53; P<2.12e-10). Similarly, the measured ICI and DCI indices are significantly correlated with memory scores measured with the Rey Auditory Verbal Leaning Test (RAVLT) delayed recall score as shown in FIG. 16B. FIG. 16B shows the relationship between the RAVLT delayed recall score and altered connectivity indices (DCI and ICI), where (RAVLT=15/(1+exp(-1.2*DC1+3.2*ICI-1.4)); F=6.70; df=2, 32; P<0.0037.

The above classification method works for a hypothesis that functional connectivity in large-scale neural networks is altered along with the disorder or disease progression, and that the functional connectivity alteration in certain networks is decreased and in other networks the functional connectivity alteration is increased. By first identifying and then quantifying the functional connectivity differences in these networks between healthy and diseased subjects, a classification for individual subjects can be made among CN, and a variety of disorders including AD and aMCI. Experimental results support this hypothesis.

In the tri-group classification scenario described above, the two-step approach may be employed. The first step may be to classify between AD and non-AD subjects (the non-AD group contains aMCI and CN subjects), and the second step may be to classify between aMCI and CN subjects. The justification to use the two-step approach is that the involved LSN functional connectivity changes between the AD and non-AD groups may be different than those between aMCI and CN groups. As the results show in FIG. 10A, 401 decreased connections that classified AD from non-AD subjects do not contain the six connections that classified aMCI from CN. In other words, the involved networks employed to classify these groups of subjects are different. Clearly, the connectivity difference between AD and non-AD is much larger than the difference between the aMCI and CN groups.

The present systems and methods demonstrate the feasibility to employ the changes in LSN connectivity to classify AD, aMCI and CN subjects. The systems and methods of the present invention may also be used to detect and predict other brain disorders as well. The invention's LSN classification method as described has numerous advantages.

First, this method does not depend on the default mode or the hippocampus hypothesis of AD progression, and thus not limit to brain regions involved. Therefore, the global LSN classification advantageously may provide high accuracy.

Second, previous studies employed dichotomous categorization based on brain atrophy to classify AD vs. CN, CN vs. MCI, or MCI vs. AD. However, in tri-group classification, such dichotomous categorization could be problematic because the classifiers obtained can be different between any two groups of subjects.

Third, in comparison with the FIB-PET method, in which the clinical symptoms were not coupled to amyloid deposition, the present LSN classification method may be configured to provide quantitative relationships between network connectivity strengths and behavioral changes. Therefore, the changes in connectivity strengths can serve as a biomarker at the preclinical stage and be employed to predict and monitor disease progression.

It is expressly contemplated that any of the processes or steps described herein may be combined, eliminated, or reordered. In other embodiments, instructions may reside in computer readable medium wherein those instructions are executed by a processor to perform one or more of processes or steps described herein. As such, it is expressly contemplated that any of the processes or steps described herein can be implemented as hardware, software, including program instructions executing on a computer, or a combination of hardware and software. Accordingly, this description is meant to be taken only by way of example, and not to otherwise limit the scope of this invention.

The foregoing has been a detailed description of illustrative embodiments of the invention. Various modifications and additions can be made without departing from the spirit and scope thereof. Furthermore, since numerous modifications and changes will readily occur to those skilled in the art, it is not desired to limit the invention to the exact construction and operation shown and described. For example, any of the various features described herein can be combined with some or all of the other features described herein according to alternate embodiments. While the preferred embodiment has been described, the details may be changed without departing from the invention, which is defined by the claims.

The invention claimed is:

1. A system for classifying the brain of a subject into a class based on presence or progression or lack of a brain disorder, the system comprising:
   a processor operable to access time course image data from a memory, the processor programmed to perform the steps of:
   a) accessing from the memory, time course image data previously acquired with a medical imaging system from the brain of the subject;
   b) generating functional connectivity data by processing the time course image data, wherein the functional connectivity data indicates correlations between neuronal activity in the brain of the subject at different functional regions of interest in a set of functional regions of interest, wherein each functional region of interest corresponds to a different anatomical region in the brain of the subject;
   c) processing the functional connectivity data with at least one class classifier, the class classifier being based on at least one of an increased functional connectivity at the set of functional regions of interest and a decreased functional connectivity at the set of functional regions of interest, wherein increased functional connectivity is characterized by connections in the set of functional regions of interest with positive correlation values above a selected threshold value of 1.96 and decreased functional connectivity is characterized by connections in the set of functional regions of interest with negative correlation values below selected threshold value of −1.96, further comprising:
      selecting a connection set comprising elements in the functional connectivity data having one of positive correlation values above the selected threshold of 1.96 or negative correlation values below the selected threshold value of −1.96;
      computing a connectivity index value by averaging the correlation values associated with the connection set; and
      processing the functional connectivity data with the at least one class classifier that implements a classification based on the connectivity index value;
   d) classifying the subject into at least one class based on step c), wherein the at least one class includes at least one of Alzheimer's disease (AD), amnestic mild cognitive impairment (aMCI), and cognitively normal (CN), and classifying the subject includes at least two steps comprising:
      d)i) classifying the subjects into an AD class or a non-AD class using an AD versus non-AD classifier; and
      d)ii) classifying the non-AD subjects into an aMCI class or a CN class using an aMCI versus CN classifier; and
   a display in communication with the processor and configured to display the functional connectivity data generated and processed by the processor in addition to an indication of the at least one class.

2. The system as recited in claim 1 in which the set of functional regions of interest comprises at least a pair of functional regions of interest.

3. The system as recited in claim 1 in which the at least one class classifier is derived by detecting corresponding changes between different classes in training data.

4. The system as recited in claim 1 in which the set of functional regions of interest correlates to neurological functional regions, with one neurological functional region being different from another neurological functional region in at least one of a shape, location, and a number of voxels included in the neurological functional region.

5. The system as recited in claim 1 in which the time course image data is acquired with a magnetic resonance imaging (MRI) system.

6. The system as recited in claim 1 in which the time course image data is acquired when the subject is in a resting state.

7. The system as recited in claim 1 in which step c) includes processing the functional connectivity data generated in step b) by processing the functional connectivity data with more than one class classifier.

8. The system as recited in claim 1 in which more than two classes are classified.

9. The system as recited in claim 8 in which not all classes are classified at the same time.

10. The system as recited in claim 1 in which step d) determining the functional connectivity in the brain of the subject comprises computing a cross-correlation between time courses in the set of functional regions of interest.

11. The system as recited in claim 1 in which the increased functional connectivity at the set of functional regions of interest and the decreased functional connectivity at the set of functional regions of interest are derived by statistical hypothesis testing between different classes.

12. The system as recited in claim 1 in which the at least one class is divided into a training cohort and a validation cohort by at least one of random sampling, bootstrapping, and leave n out methods.

13. The system as recited in claim 1 in which the processor is programmed to perform step c) by:
   selecting the connection set as a decreased connection set comprising elements in the functional connectivity data having negative correlation values higher than the selected threshold value;
   computing the connectivity index value as a decreased connectivity index (DCI) by averaging the negative correlation values associated with the decreased connection set; and
   processing the functional connectivity data with the at least one class classifier that implements a classification based on the DCI; and
wherein the display is configured to display the functional connectivity data in a manner that visually indicates the decreased connection set as connected regions having decreased functional connectivity.

14. The system as recited in claim 1 in which the processor is programmed to perform step c) by:
   selecting the connection set as an increased connection set comprising elements in the functional connectivity data having positive correlation values higher than the selected threshold value;
   computing the connectivity index value as an increased connectivity index (ICI) by averaging the positive correlation values associated with the increased connection set; and
   processing the functional connectivity data with the at least one class classifier that implements a classification based on the ICI; and
wherein the display is configured to display the functional connectivity data in a manner that visually indicates the increased connection set as connected regions having increased functional connectivity.

15. A method for classifying a subject into one or more classes based on the presence or progression or lack of a brain disorder, the step comprising:
- a) acquiring with a medical imaging system time course image data from the brain of the subject;
- b) generating functional connectivity data with a processor by processing the time course image data, wherein the functional connectivity data indicates correlations between neuronal activity in the brain of the subject at different functional regions of interest in a set of functional regions of interest, wherein each functional region of interest corresponds to a different anatomical region in the brain of the subject;
- c) processing the functional connectivity data with at least one class classifier implemented in the processor, the class classifier being based on at least one of an increased functional connectivity at the at least a set of functional regions of interest and a decreased functional connectivity at the at least a set of functional regions of interest, wherein increased functional connectivity is characterized by connections in the set of functional regions of interest with positive correlation values above a selected threshold value of 1.96 and decreased functional connectivity is characterized by connections in the set of functional regions of interest with negative correlation values below a selected threshold value of −1.96 further comprising:
  - selecting a connection set comprising elements in the functional connectivity data having one of positive correlation values above the selected threshold value of 1.96 or negative correlation values below the selected threshold value of −1.96;
  - computing a connectivity index value by averaging the correlation values associated with the connection set; and
  - processing the functional connectivity data with the at least one class classifier that implements a classification based on the connectivity index value;
- d) classifying the subject into at least one class based on step c) using the processor, wherein the at least one class includes at least one of Alzheimer's disease (AD), amnestic mild cognitive impairment (aMCI), and cognitively normal (CN), and classifying the subject includes at least two steps comprising:
  - d)i) classifying the subjects into an AD class or a non-AD class using an AD versus non-AD classifier; and
  - d)ii) classifying the non-AD subjects into an aMCI class or a CN class using an aMCI versus CN classifier; and
- e) displaying the functional connectivity data to a user in addition to an indication of the at least one class.

16. The method as recited in claim 15 in which step c) includes:
- selecting the connection set as a decreased connection set comprising elements in the functional connectivity data having negative correlation values higher than the selected threshold value;
- computing the connectivity index value as a decreased connectivity index (DCI) by averaging the negative correlation values associated with the decreased connection set; and
- wherein the class classifier implements a classification based on the DCI; and wherein the functional connectivity data displayed to the user visually indicates the decreased connection set as connected regions having decreased functional connectivity.

17. The method as recited in claim 15 in which step c) includes:
- selecting the connection set as an increased connection set comprising elements in the functional connectivity data having positive correlation values higher than the selected threshold value;
- computing the connectivity index value as an increased connectivity index (ICI) by averaging the positive correlation values associated with the increased connection set; and
- wherein the class classifier implements a classification based on the ICI; and wherein the functional connectivity data displayed to the user visually indicates the increased connection set as connected regions having increased functional connectivity.

* * * * *